United States Patent [19]

Marotti et al.

[11] Patent Number: 5,106,741
[45] Date of Patent: Apr. 21, 1992

[54] TISSUE PLASMINOGEN ACTIVATOR (TPA) ANALOGS

[75] Inventors: Keith R. Marotti; Edward F. Rehberg; Nicole Y. Theriault, all of Kalamazoo, Mich.

[73] Assignee: The Upjohn Company, Kalamazoo, Mich.

[21] Appl. No.: 714,365

[22] Filed: Jun. 12, 1991

Related U.S. Application Data

[63] Continuation of Ser. No. 23,491, Jan. 28, 1987, abandoned, which is a continuation-in-part of Ser. No. 909,482, Sep. 19, 1986, abandoned, which is a continuation-in-part of Ser. No. 811,607, Dec. 20, 1985, abandoned.

[51] Int. Cl.$^5$ .................. C12N 9/64; C12N 15/58
[52] U.S. Cl. .................. 435/226; 435/172.3; 435/212; 435/240.2; 435/252.33; 435/252.3; 435/255; 435/320.1; 536/27; 935/14; 935/28; 935/29; 935/32; 935/69; 935/70; 935/73
[58] Field of Search .................. 435/226, 212, 240.2, 435/255, 172.3, 252.33, 252.3, 320.1; 536/27; 935/14, 28, 29, 32, 69, 70, 73

[56] References Cited

FOREIGN PATENT DOCUMENTS 0093619 11/1983 European Pat. Off. .......... 435/226
143081 11/1984 European Pat. Off. .
196920 4/1986 European Pat. Off. .
0207589 1/1987 European Pat. Off. .......... 435/226

OTHER PUBLICATIONS

Barany et al., in the Peptides: Analysis, Synthesis, Biology, Eds. Gross and Meienhofer, Academic Press, vol. II, Chapter 1, pp. 5, 7, 17, 32–34 (1979).
Nan Zonneveld et al., International Congress for Society on Thrombosis and Haemeostasis, Abstract 022, Jul. 15, 1985.
Rothstein, R. et al., Methods in Enzymology, vol. 68, pp. 98–109, 1979.
Smith, G. et al., *Molec and Cell. Biology*, vol. 3, pp. 2156–2165, 1983.
Rijken, D. C. et al., Purification and Characterization of the Plasminogen Activator Secreted by Human Melanoma Cells in Culture, J. Biol. Chem., 256(13):7035–7041 (Jul. 10, 1981).
Kluft, C. et al., Large-Scale Production of Extrinsic (Tissue-Type) Plasminogen Activator from Human Melanoma Cells, Advances in Biotechnological Processes, Eds. Mizrahi, A. et al., 2:97–110 (1983).
Korninger, C. et al., Thromboylsis with Human Extrinsic (Tissue-Type) Plasminogen Activator in Dogs with Femoral Vein Thrombosis, J. Clin. Invest., 69:573–580 (Mar. 1982).
Weimar, W. et al., Specific Lysis of an Iliofemoral Thrombus by Administration of Extrinsic (Tissue-Type) Plasminogen Activator, The Lancet, pp. 1018–1020 (Nov. 7, 1981).
Van De Werf, F. et al., Coronary Thrombolysis with Tissue-Type Plasminogen Activator in Patients with Evolving Myocardial Infarction, The New England J. of Medicine, 310(10):609–613 (Mar. 8, 1984).
Collen, D. et al., Clot-Selective Coronary Thrombolysis with Tissue-Type Plasminogen Activator, Science, 220:1181–1183 (Jun. 10, 1983).
Rijken, D.C. et al., Fibrinolytic Properties of One-Chain and Two-Chain Human Extrinsic (Tissue-Type) Plasminogen Activator, J. Biol. Chem., 257(6):2920–2925 (1982).
Korninger, C. et al., Studies on the Specific Fibrinolytic Effect of Human Extrinsis (Tissue-Type) Plasminogen Activator in Human Blood and in Various Animal Species in Vitro, Thrombos. Haemostas., 46(2):561–565 (1981).
Banyai, L. et al., Common Evolutionary Origin of the Fibrin-Binding Structures of Fibronectin and Tissue-Type Plasminogen Activator, FEBS Lett., 163(1):37–41 (Oct. 1983).
Ny, T. et al., The Structure of the Human Tissue-Type Plasminogen Activator Gene: Correlation of Intron and Exon Structures to Functional and Structural Domains, Proc. Natl. Acad. Sci., USA 81:5355–5359 (Sep. 1984).
Opdenakker, G. et al., Messenger RNA for Human Tissue Plasminogen Activator, Eur. J. Biol., pp. 269–274 (1982).
Pennica, D. et al., Cloning and Expression of Human Tissue-Type Plasminogen Activator cDNA in *E. coli*, Nature, 301:214–221 (1983).
U.S. Patent Application, Ser. No. 663,025, filed 10-1-9-84, pending.
Vergeijen, J. H. et al., Involvement of Finger Domain and Kringle 2 Domain of Tissue-Tpye Plasminogen Activator in FIbrin Binding and Stimulation of Activity by Fibrin, The EMBO Journal, 5(13):3525–3530 (1986).
van Zonneveld, A. J. et al., On the Interation of the Finger and the Kringle-2 Domain of Tissue-Type Plasminogen Activator with Fibrin, J. Biol. Chem., 261(30):14214–14218 (Oct. 25, 1986).

(List continued on next page.)

*Primary Examiner*—Richard A. Schwartz
*Assistant Examiner*—Nancy Treptow
*Attorney, Agent, or Firm*—Mark DeLuca; Debbie K. Wright

[57] ABSTRACT

This invention discloses human tissue plasminogen activator (TPA) analogs. The analogs are TPA-like molecules that have had the native domain regions either rearranged, deleted, added or a combination thereof. The analogs are the product of the expression of recombinant DNA also described herein. Additonally, the present invention described replication and expression plasmids containing the TPA-coding DNA sequences described above and suitable host microorganisms that are capable of expressing the TPA analogs after becoming transformed with an appropriate plasmid.

6 Claims, No Drawings

OTHER PUBLICATIONS

Van Zonneveld, A. J. et al., Autonomous Functions of Structural Domains on Human Tissue-Type Plasminogen Activator, Proc. Natl. Acad. Sci., USA, 83:4670–4674 (Jul. 1986).

Bang, N. U. et al., Functional Properties of Tissue Plasminogen Activator Mutants, Blood, 66(5), Suppl. 1, Abstract 1205, p. 330a (Nov. 1985).

Bang, N. U. et al., Tissue Plasminogen Activator Structure-Function Relationships, Clin. Res., 33(4), 878A (1985).

Tiemeier, D. et al., Structure:Function Studies of Tissue-Type Plasminogen Activator, Fed. Proc. 45(4), Abstract 4702, p. 963 (1986).

TISSUE PLASMINOGEN ACTIVATOR (TPA) ANALOGS

CROSS-REFERENCE

This application is a file wrapper continuation of application Ser. No. 07/023,491 filed Jan. 28, 1987, which is now abandoned, a continuation-in-part of application Ser. No. 909,482 filed 19 September 1986, abandoned; which is a continuation-in-part of application Ser. No. 811,607 filed 20 December 1985, abandoned.

BACKGROUND OF THE INVENTION

1. Field of the Invention.

This invention discloses human tissue plasminogen activator (TPA) analogs. The analogs are TPA-like molecules that have had the native domain regions either rearranged, deleted, added or a combination thereof. The analogs are the product of the expression of recombinant deoxyribonucleic acid (DNA) also described herein. Additionally, the present invention describes replication and expression plasmids containing the TPA-coding DNA sequences described above and suitable host microorganisms that are capable of expressing the TPA analogs after becoming transformed with an appropriate plasmid.

2. Background

TPA has therapeutic value in treating blood clots by helping dissolve the clots as they form. Thrombolysis is the process of fibrin clot dissolution. For that purpose the serine protease plasmin is formed from its inactive zymogen, plasminogen. Activation of plasminogen is achieved through proteolytic cleavage by a class of serine proteases called plasminogen activators. These activators are present in most body fluids and initiate the activation of plasminogen to plasmin. This sets up a cascade whereby a small amount of plasminogen activator can initiate the activation of a large amount of plasminogen. In vivo, the plasminogen activator activates plasminogen to plasmin which then acts to degrade the fibrin clot. The plasminogen activator which is physiologically important to clot lysis is TPA.

TPA is a serine protease with a molecular weight of approximately 66,000 daltons which is produced by the vascular endothelial cells. It is glycosylated and its only known protein substrate is plasminogen. TPA has five domains: the fibronectin finger domain (F), the growth factor domain (G), the kringle 1 domain (K1), the kringle 2 domain (K2) and the active site domain (A). One or more of these domains is responsible for the unique fibrin binding activity of TPA.

In addition to its fibrin affinity, TPA activation of plasminogen is enhanced in the presence of fibrin. These properties make TPA a valuable therapeutic agent because other clot dissolving drugs such as urokinase or streptokinase do not have any specificity for the fibrin clot.

By manipulating the domains it is possible to improve the affinity of the native enzyme for the fibrin and increase its in vivo half-life. More specifically, duplication of the Kringle 2 or Finger domain will enhance fibrin affinity. Elimination of the growth factor domain will enhance in vivo half-life and places the finger region domain next to the kringle regions 1 or 2 to increase fibrin affinity. Information Disclosure.

Human TPA has been purified and its physical characteristics have been studied. Rijken et al. "Purification and Characterization of the Plasminogen Activator Secreted by Human Melanoma Cells in Culture", J. Biol. Chem., vol. 256, no. 13, pp. 7035–41 (July 10, 1981). Experimental quantities of human TPA are obtainable from the culture medium of human melanoma cells. Kluft, C. et al., "Large-scale production of extrinsic (tissue-type) plasminogen activator from human melanoma cells" in Advances in Biotechnological Processes, Eds. Mizrahi, A. and Wezel, A. L. 2:97–110 (1983). The bioactivity of human TPA has been studied, and it has been demonstrated to have therapeutic value in animal models and in humans through its ability to dissolve life-threatening blood clots. Korninger et al., "Thrombolysis with Human Extrinsic (Tissue-type) Plasminogen Activator in Dogs with Femoral Vein Thrombosis", J. Clin. Invest., vol. 69, pp. 573–580 (March, 1982); Weimar et al., "Specific Lysis of an Iliofemoral Thrombus by Administration of Extrinsic (Tissue-type) Plasminogen Activator", The Lancet, pp. 1018.20 (Nov. 7, 1981); and Van De Werf, F. et al., Coronary Thrombolysis with Tissue-type Plasminogen Activator in Patients with Evolving Myocardial Infarction, J. of N. Eng. Med., 310:609–613 (1984). The half-life of TPA is estimated at 2–3 minutes making it inconvenient, if not impractical, to use as a therapeutic agent. Collen, D. et al., Clot-selective Coronary Thrombolysis with Tissue-type Plasminogen Activator, Science, 220: 1181–1183 (1983).

The enzyme kinetics of TPA have been studied. Rijken et al., "Fibrinolytic Properties of One-Chain and Two-Chain Human Extrinsic (Tissue-type) Plasminogen Activator", J. Biol. Chem., vol. 257:2920–2925 (1982). The binding and fibrolytic affinity of human TPA for human blood clots over the blood clots of other animals is known. Korninger et al., "Studies on the Specific Fibrinolytic Effect of Human Extrinsic (Tissue-type) Plasminogen Activator in Human Blood and in Various Animal Species in Vitro", Thrombos. Haemostas., 46(2): 561–565 (1981). The structural relationship of domains with the fibrinolytic activity and affinity has also been delineated. Banyai, L. et al., Common evolutionary origin of the fibrin-binding structures of fibronectin and tissue-type plasminogen activator, FEBS Lett. 163(1):37–41 (1983) and Ny, T. et al,. The Structure of the Human Tissue-type Plasminogen Activator Gene: Correlation of Intron and Exon Structures to Functional and Structural Domains, Proc. Natl. Acad. Sci. USA 81:5355–5359 (1984).

The expression of TPA by transformed bacteria and yeast is also known. The messenger ribonucleic acid (RNA) of human TPA was first isolated in 1982. Opdenakker et al., "Messenger RNA for Human Tissue Plasminogen Activator", Eur. J. Biol., pp. 269–74 (1982). Bacteria were transformed for expression of TPA by Pennica et al., "Cloning and Expression of Human Tissue-type Plasminogen Activator cDNA in E. coli.", Nature, 301:214–21 (1983). Procedures to transform yeast to express human TPA have been described in U.S. patent application Ser. No. 663,025 and published European patent application EP 143,081.

There have been several recent reports of domain deletions of TPA in the literature using recombinant technology or other enzymatic techniques. A discussion of these reports is offered but the inventors do not concede that these references are prior art under 35 USC 102 at this time and provide them in order to offer a complete background of this invention. The first studies take advantage of native restriction sites to delete sections of the TPA protein. J. H. Verheigen, et al., Involvement of finger domain and kringle of tissue-type plasminogen activator in fibrin binding and stimulation of activity by fibrin, EMBO Journal Vol. 5 No. 13:3525–3530 (1986); A. J. van Zonneveld, et al., On the Interaction of the finger and the kringle-2 domain of tissue-type plasminogen activator with fibrin, J. Biol. Chem. Vol. 261 No. 30:14214–14218 (1986) and A. J. van Zonneveld, et al., Autonomous functions of structural domains on human tissue-type plasminogen activator, Proc. Natl. Acad. Sci. USA 83: 670–4674 (1986). There are several abstracts indicating mutants of TPA but they do not offer sufficient methodology to discern whether they have indeed disclosed deletions of the nature described herein. N. U. Bangs, et al., Functional properties of tissue plasminogen activitor mutants, Blood 66(5) Suppl. 1 Asbstract 1205 page 330a (1985); N. U. Bangs, et al., Tissue plasminogen structure-function relationships, Clin. Res. Vol.33 No.4 878A, (1985) and D. Tiemeier, et al., Structure:function studies of tissue-type plasminogen activator, Fed. Proc. 45 (4) Abstr. 4702 page 963 (1986). Others have made deletions through enzymatic degradation processes. EP 196920-A Degraded species of tissue-type plasminogen activator—useful in treating thrombotic disease and having a reduced clearance rate in vivo.

SUMMARY OF THE INVENTION

This invention relates to the improved pharmacological effects of native human tissue plasminogen activator through the rearranging of the domain regions of the protein by genetic recombination. The improved effects include a longer half-life and increased fibrin affinity. Disclosed herein are DNA sequences that contain unique restriction sites within the interdomain regions of TPA useful for convenient splitting and rearranging of the domains. Plasmids containing this TPA coding DNA and suitable hosts for expressing the rearranged TPA are also disclosed. Finally the rearranged TPA proteins are described.

Specifically this invention describes a DNA compound consisting of nucleotide bases coding for TPA-like proteins comprising an active site and one or more domains selected from the group comprising the finger domain (F), the growth factor domain (G), the kringle 1 domain (K1) and the kringle 2 domain (K2) wherein the DNA compound: (a) contains within the nucleotide sequences encoding the interdomain regions non-native endonuclease restriction sites that are not present in the nucleotide sequences encoding the domain regions and (b) encodes a TPA-like protein having a molecular weight less than 90,000 daltons and in which no domain appears more than twice.

More specifically, there are disclosed herein compounds of the above TPA-coding DNA in which an Xba site is inserted between nucleotide bases 187 to 198, in which an HpaI or SphI site or combination thereof is inserted between nucleotide bases 328 to 342, in which an EcoRV, ClaI, or SmaI site or combination thereof is inserted between nucleotide bases 442 to 462, in which an BamHI or HpaI site or combination thereof is inserted between nucleotide bases 709 to 726, and in which an MstI. SphI, or XmaIII site or combination thereof is inserted between nucleotide bases 973 to 997.

Among those TPA-coding DNA sequences described above are those in which the sequence of nucleotides coding for domain regions has been altered from the native arrangement with respect to their order, occurrence or both. More specifically, there is described herein TPA coding DNA sequences in which the DNA codes for TPA-like proteins in which the domains are ordered as follows from the amino terminal end: (1) multiple domain deletions—FA, K2A, FK1A, FK2A, FGA, K1K2A., (2) single domain deletions—FGK1A, FGK2A, FK1K2A, GK1K2A; (3) combinations of domain deletions and substitutions—FK2K2A, FGK2K2A, FGK1K1A, FGK2K1A, FFK1K2A; (4) the native order of domains—FGK1-K2A; and (5) the addition of a second finger domain FFGK1K2A.

In addition there are compounds of TPA-coding DNA sequences as described above in which the sequences of nucleotides both upstream and downstream from the sequences encoding the TPA-like protein render the compound capable of being maintained in a suitable host cell. More specifically there are described herein such compounds that are also capable of permitting a suitable host cell to express TPA-like proteins especially those analogs in which the domain regions have been altered in their order, occurrence or both provided that the overall molecular weight of the expressed protein does not exceed 90,000 daltons and no domain appears more than twice. Even more specifically, there is described herein expression and replication plasmids (vectors) containing DNA coding for TPA-like proteins in which the domains are ordered as follows from the amino terminal end: (1) multiple domain deletions FA. K2A, FGA, K1K2A; (2) single domain deletions—FGK1A, FGK2A; (3) combinations of domain deletions and substitutions—FK2K2A, FGK2K2A, FGK1K1A, FGK2K1A, FFK1K2A; (4) the native order of domains—FGK1K2A; and (5) the addition of a second finger domain—FFGK1K2A.

Suitable host microorganisms capable of maintaining the above described plasmids and for the expression of the rearranged TPA proteins are also described herein. For example there is described herein expression and non-expression vectors containing DNA sequences coding for TPA-like proteins in which the suitable host is selected from the group consisting of: (a) yeast; (b) Escherichia sp.; and, (c) cell cultures. More specifically, there is described herein a preferred expression vector containing DNA sequences coding for TPA-like proteins in which the suitable host cell is a Chinese hamster ovary (CHO) cell.

Finally there are described herein compounds of TPA-like proteins consisting of an active site (A) and one or more domains selected from the group consisting of the finger domain (F), the growth factor domain (G), the kringle 1 domain (K1), and the kringle 2 domain (K2) wherein the domain regions have been altered from the native arrangement with respect to their order, occurrence or both provided that the overall molecular weight of the expressed protein does not exceed 90,000 daltons and no domain appears more than twice. The following arrangements of TPA domains are preferred: (1) multiple domain deletions—FA, K2A, FK1A, FK2A, FGA, K1K2A; (2) single domain deletions FGK1A, FGK2A, FK1K2A, GK1K2A; (3) combinations of domain deletions and substitutions FK2K2A, FGK2K2A, FGK1K1A, FGK2K1A, FFK1K2A; and (4) the addition of a second finger domain—FFGK1-K2A.

DETAILED DESCRIPTION

This invention involves a series of molecular genetic manipulations that can be achieved in a variety of known ways. Two prototype genes having unique endonuclease restriction sites between the domains of TPA have been deposited in accordance with the Budapest Treaty. The host microorganisms are *E. coli* strains containing plasmids designated pTPA-B1,2,3.4(a) and pTPA-B1,2,3,4 and illustrated in Charts 10 and 11, respectively. The deposit of pTPA-B1,2,3,4(a) was made with the Northern Regional Research Center, Peoria, Ill., USA on Aug. 29, 1986 and assigned Accession Number NRRL B-18106. The deposit of pTPA-B1,2,3,4 was made with the Northern Regional Research Center, Peoria, Ill., USA on Nov. 28, 1986 and assigned Accession Number NRRL B-18142.

The deposited plasmid should not be construed as a limitation of this invention in any manner. Although a convenient starting material, the following will detail various methods available to create the TPA analogs from alternative starting materials and is followed by specific examples of preferred methods.

In summary the necessary genetic manipulations can be described as the obtaining of a dDNA of TPA, the synthesizing of blocks of oligonucleotides containing the coding sequence of the various TPA domains with selected restriction sites in the interdomain regions, the cloning and replication of the domains in *E. coli* and the expression of the desired TPA analog.

A. DESCRIPTION OF THE TABLES

Table 1 shows the results of in vitro tests of activity and antibody recognition for TPA analogs.

Table 2 illustrates the specific sequence and base numbering positions for synthetic TPA DNA compared to the native cDNA. The native domains are all present in their natural order in Table 2. Table 3 compares the amino acid sequence of the native TPA to a TPA analog having all the natural domains in their normal order (see chart 11). In both tables the top sequences present the native sequence of either nucleotides or amino acids with the lower sequences reflecting the modified TPA. Table 4 presents the oligonucleotides used to synthetically build the TPA analogs. Table 5 compares the native TPA protein to the the analog described in chart 11 containing the native order of TPA domains by illustrating the amino acids and nucleotides contained within the domain regions. The interdomain regions are those amino acids lying between the domains as delineated in Table 5 (see Definitions). Throughout this document, the numbered references to either nucleotides or amino acids refer to these tables.

B. GENERAL METHODS

Generally, the nomenclature and general laboratory procedures required in this application can be found in Maniatis, T. et al., Molecular Cloning A Laboratory Manual. Cold Spring Harbor Laboratory. Cold Spring Harbor, New York, 1982. The manual is hereinafter referred to as Maniatis.

All *E. coli* strains are grown on Luria broth (LB) with glucose, Difco's Antibiotic Medium #2 and M9 medium supplemented with glucose and acid-hydrolyzed casein amino acids. Strains with resistance to antibiotics were maintained at the drug concentrations described in Maniatis. Transformations were performed according to the method described by Morrison, D. A. (1977), J. of Bact., 132:349–351; or by Clark-Curtiss, J. E. and Curtiss, R., 1983, in Methods in Enzymology, 101:347–362, Wu, R., Grossman, L. and Moldave, K., eds., Academic Press, New York.

All enzymes were used according to the manufacturer's instructions. Colony hybridization is carried out as generally described in Grunstein, M. et al., Proc. Nat. Acad. Sci., 72, vol. 72. pp. 3961-5 (1975) but modified to provide the following method: Nitrocellulose filters are made which contain colonies of the cells prepared above. The filters are then laid, colony-side up, onto a bed of 5–8 thickness of Whatman 3MM paper soaked in denaturing solution consisting of 1.5 M NaCl, 0.5 M NaOH. The denaturant is allowed to diffuse upwards into the colonies for 1.5-2 minutes at which time the filters are transferred to a second bed of 3MM papers soaked in neutralizing solution containing 0.5 M Tris HCl pH 7.4, 2×SSC (1×SSC = 0.15 M NaCl., 0.015 M Na Citrate; pH 7.1), and 25 mM EDTA, for 1–3 minutes. Filters are then thoroughly air dried and baked in vacuo for 2–4 hours at 80° C.

Hybridization conditions for oligonucleotide probes are as previously described by Goeddel, D. V. et al., Nature, vol. 290, pp. 20–26 (1981).

After hybridization, the probe containing solution is removed and saved and the filters are washed in 0.1% SDS, 0.2×SSC for a total of 3 hours with 5 changes of 400 ml each. Filters are thoroughly air dried, mounted, and autoradiographed using Kodak X-OMAT AR film and Dupont Cronex Lightnening Plus intensifying screens for 16 hours at −70° C.

For sequencing of plasmids, minipreps of plasmid DNA are prepared according to the method of Holmes, D. S. et al., Analyt. Biochem., vol. 114, p. 193 (1981). Dideoxy sequencing is carried out according to Sanger F. et al., "Cloning in single stranded bacteriophage as an aid to rapid DNA sequencing", J. Mol. Biol. 143:161–178 (1977). The dideoxy containing reactions are prepared for electrophoresing by heating to 90° for 2 min. and quenching on ice. 2-3 μl per lane is loaded on an 8% sequencing denaturing polyacrylamide gel prepared and ran according to Sanger and Coulson, "The use of thin acrylamide gels for DNA sequencing", FEBS Lett. 87:107–110, (1978). The gels are exposed at room temperature for 2–4 days, and films (Kodak XAR-5) are developed as per manufacturers' recommendations.

Nucleotide sizes are given in either kilobases (kb) or basepairs (bp). These are estimates derived from agarose gel electrophoresis.

C. TPA cDNA

TPA cDNA was a convenient source of the active site portion of the nucleic acid sequence. Therefore it was unnecessary to chemically synthesize the active site. TPA cDNA is available from a number of sources. Workers have reported preparing portions of the TPA cDNA from messenger RNA isolated from cell cultures producing large amount of TPA specifically Bowes Melanoma cells. Edlund et al., "Isolation of cDNA Sequences Coding for a Part of Human Tissue Plasminogen Activator", vol. 80, pp. 349–352 (Jan. 1983)., Gronow et al., "Production of Human Plasminogen Activators by Cell Culture", Trends in Biotechnology, vol. 1, no. 1, pp. 26–29 (1983); and Pennica et al., "Cloning and Expression of Human Tissue-type Plasminogen Activator cDNA in *E. coli.*", Nature, vol. 301, pp. 214-21 (20 Jan. 1983).

More specifically, Genentech, Inc., filed a European patent application No. 0093619 on 4 May 1983, relying on the priority applications having U.S. Ser. Nos. 374,860; 398,003 and 483,052 having the respective filing dates of May 5, 1982; July 14, 1982 and Apr. 7, 1983 which is hereinafter referred to as the Genentech Application. The Genentech Application discloses *E. coli* K12 strain 294 with ATCC No. 31446, that is a transformant having a recombinant DNA compound coding for TPA. Additionally, the *E. coli* K12 strain as ATCC No. 27325 from which extracts of a TPA are also prepared for assay of fibrinolytic activity. Thus, the disclosures include a recombinant DNA compound useful herein. Likewise, disclosure of the Genentech Application provides DHFR+ CHO-KI (ATCC CL 61) cells transformed for amplification also expressing TPA. Thus, again the deposit, ATCC CL61 discloses recombinant DNA nucleotides coding for TPA useful herein.

The disclosure herein of Preparation 2 provides one of skill in the art with an isolation process from among the processes known in the art applicable to the Bowes melanoma cell for obtaining the recombinant DNA compound coding for a TPA. The Bowes melanoma cell is commonly available to the public.

D. SYNTHESIZING THE TPA DOMAINS.

As noted above, portions of the TPA analog DNA sequences were prepared from cDNA; however, most of the sequence and even the entire sequence could have been created synthetically. Cost and convenience are the controlling parameters in deciding how to create a particular TPA analog's sequence. By selecting restriction sites not found in the TPA domains of the desired analog and by inserting these restriction sites within the interdomain regions of TPA, one avoids digesting a desired part of the TPA DNA sequence and allows for the easy removal and insertion of each individual domain.

By chemically synthesizing a portion of the TPA gene, one can decide on a base by base process which nucleotides are to be used. The following advantages arise from this process: (1) the minimization of secondary structure in the transcription product; (2) the minimization of AT-GC regions of self-complementarity; and, (3) the placement of unique restriction sites at desirable locations along the cDNA sequence.

Oligonucleotides are chemically synthesized according to the solid phase phosphoramidite triester method first described by Beaucage S. L. and Caruthers, M. H. Tetrahedron Letts. 22(20):1859-1862 (1981) using an automated synthesizer, as described in Needham-VanDevanter, D. R., et al., Nucleic Acids Res., 12:6159-6168 (1984). Purification of oligonucleotides was by either native acrylamide gel electrophoresis or by anion-exchange HPLC as described in Pearson, J. D. and Regnier, F. E., J. Chrom., 255:137-149 (1983).

Oligodeoxynucleotides are chemically synthesized in lengths of less than 40 nucleotides. Each fragment is designed to be complementary to its corresponding complementary strand and each double stranded segment contains sticky ends to optimize ligation. The following criteria are considered in the division of the DNA for synthesis of the fragments: 1) The length of the oligonucleotide fragments should be less than 40 bases in length for the ease in chemical synthesis and purification. 2) A minimal of 6 bases "protruding" from the complementing "top" and "bottom" oligonucleotide fragments appears to allow optimal alignment and ligation of the segments. 3) Regions of four bases or more which can associate with either the primary or the complement sequence should be avoided.

The sequence of the synthetic oligonucleotides can be verified using the chemical degradation method of Maxam, A. M. and Gilbert, W., Grossman, L. and Moldave, D., eds., Academic Press, New York, Methods in Enzymology, 65:499-560 (1980). Alternatively, the sequence can be confirmed after the assembly of the oligonucleotide fragments into the double-stranded DNA sequence using the method of Maxam and Gilbert, supra, or the chain termination method for sequencing double-stranded templates of Wallace, R. B., et al., Gene, 16:21-26 (1981).

Eighty-seven separate oligonucleotides (Table 4) were synthesized. The specific assembly strategy disclosed herein was to engineer the first 1099 base pairs coding for the 5' portion of the TPA analog having the selected restriction sites indicated in Chart (11). This synthetic oligonucleotide is then joined to the 3' portion of TPA cDNA at the EcoRI site at position 1287 containing the active site.

To assemble the oligonucleotide fragments into the double-stranded DNA, one can mix all of the 87 fragments together for annealing and ligation. For more efficient ligation, it is better to divide the oligonucleotides into four blocks. After ligation and purification of each block, the four blocks can then be annealed and ligated to yield the final product. Purification of the assembled blocks and the final product can be performed by acrylamide gel electrophoresis as described in Maniatis. To carry out the annealing and ligation, the general methods described in Maniatis are also used.

It may be necessary to provide an initiation codon for the synthetic TPA genes. For purposes of the *E. coli* system, the initiating codon ATG for coding for F-met is required. The initiating codon can be incorporated into the synthetic gene or be provided by the desired expression plasmid. In addition to an initiation codon, it is, for *E. coli,* convenient to incorporate into the synthetic gene of TPA a sequence that provides adequate spacing between the Shine-Dalgarno region and the initiation codon.

Proper selection of the sequence will minimize secondary structure that would otherwise interfere with transcription and translation, incorporate maximal codon usage (Grosjean H. and Fiers. W., Gene, 18:199-209. 1982); and satisfy the statistical biases found in the sequence around the ribosome binding site (Gold. L., et al., Ann. Rev. Microbiol., 35:365-403, 1981). The specific sequence for this invention is described herein by its actual sequence. However it is understood that alternative sequences could be used to optimize the expression of TPA analogs in different host cells.

E. CLONING AND CDNA AND SYNTHETIC PORTIONS OF THE TPA GENE

Methods used to clone the cDNA and the synthetic portions of TPA for replication of the recombinant fragments coding for portions of TPA are standard procedures known in the art. The Maniatis manual containing methodology sufficient to conduct all subsequently described clonings. All clonings were done in transformed *E. coli* with any well characterized strain being useful. Strain HB101 is preferred unless otherwise stated.

Cloning vectors useful for transforming *E. coli* include pBR322 and pKC7.

F. INSERTION OF UNIQUE RESTRICTION SITES IN THE DNA-CODING TPA.

The specific restriction sites chosen for the interdomain regions of TPA are illustrated in Charts 10 and 11. These are not the only restriction sites that would be useful in this invention. Restriction sites are chosen on the basis of their being unique in the TPA cDNA. Sites that will introduce minimal amino acid changes in the interdomain regions are preferred and those that are silent with respect to amino acid changes are most preferred (see Tables 1 and 2). Multiple sites having different reading frames within an interdomain are useful in order to ensure that the domains are in phase after ligation to other domains for purposes of expression. Duplicate restriction sites can be eliminated by simply digesting the site and ligating after making the ends blunt ended. The introduction of a unique site can be engineered in by chemical synthesis, commercially available linkers or by single site mutation.

The native TPA cDNA does not contain sites recognized by the following endonuclease restriction enzymes in addition to those sites engineered into the two prototype cDNA of TPA illustrated in Charts 10 and 11:

| ACC 1 | AFL 2 | AFL 3 | AHA 3 |
|-------|-------|-------|-------|
| ASU 2 | AVA 3 | AVR 2 | BCL 1 |
| BGL 1 | BSS H2 | HIND 3 | KPN 1 |
| MLU 1 | MST 2 | NAE 1 | NCO 1 |
| NDE 1 | NHE 1 | NOT 1 | NRU 1 |
| NSI 1 | PVU 1 | SAC 2 | SAL 1 |
| SAU 1 | SFI 1 | SNA 1 | SNA B1 |
| SPE 1 | XHO 1 | | |

G. EXPRESSION OF TPA ANALOGS IN *E. COLI.*

To obtain high level expression of a cloned gene, e.g., the modified TPA gene, in a prokaryotic system, it is essential to construct expression vectors which contain, at the minimum, a strong promoter to direct mRNA transcription, a ribosome binding site for translational initiation and transcription terminator. Since the accumulation of large amounts of a gene product often inhibits cell growth and sometimes causes cell death, the promoter chosen to direct the synthesis of the product must be regulated in such a way that cell growth can be allowed to reach high densities before the induction of the promoter. Examples of regulatory regions suitable for this purpose are the promoter and operator region of the *E. coli* tryptophan biosynthetic pathway as described by Yanofsky, C., Kelley, R. L. and Horn, V., J. Bacteriol., 158:1018–1024 (1984) and the leftward promoter of phage lambda ($P_L$) as described by Herskowitz, I. and Hagen, D., Annu. Rev. Genet., 14:399–445 (1980). The TPA produced in *E. coli* does not fold properly due to the large number of cysteine residues. The *E. coli*-produced TPA must first be denatured and then renatured. This can be accomplished by solubilizing the *E. coli*-produced TPA in guanidine HCl and reducing all the cystine residues with $\beta$-mercaptoethanol. The protein is then renatured either by slow dialysis or by gel filtration. U.S. Pat. No. 4,511,503.

H. EXPRESSION OF TAP ANALOGS IN YEAST.

The expression of heterologous proteins in yeast is well known. Methods in Yeast Genetics, Sherman, F., et al., Cold Spring Harbor Laboratory. (1982) is a well recognized work describing the various methods useful for producing TPA analogs in yeast.

For high level expression of a gene in yeast, it is essential to connect the gene to a strong promoter system as in the prokaryote and to also provide efficient transcription termination/polyadenylation sequences from a yeast gene. Examples of useful promoters include GAL1,10 (Johnston M., and Davis, R. W., Mol. and Cell. Biol., 4:1440–48, 1984), ADH2 (Russell, D., et al., J. Biol. Chem. 258:2674–2682, 1983), PHO5 (EMBOJ. 6:675–680, 1982), and MFα1. A multicopy plasmid with a selective marker such as Lue-2, URA-3, Trp-1, and His-3 is also desirable.

When cells are grown on glucose, GAL and ADH2 promoters are repressed, thus, allowing cells to be grown to a high density. Whereas the GAL promoters can be turned on by transferring cells to galactose medium, ADH2 will be turned on after all the glucose has been utilized by the cells. The PHO5 promoter can be switched on or off by manipulations of phosphate concentration in the medium. The MFα1 promoter in a host of the a mating-type is on all the time, but is off in diploids or cells with the a mating-type. It can, however, be regulated by raising or lowering temperature in hosts which have a ts mutation at one of the SIR loci. The effect of such a mutation at 35° C. on an α type cell is to turn on the normally silent gene coding for the a mating-type. The expression of the silent a mating-type gene, in turn, turns off the MFα1 promoter. Lowering the temperature of growth to 27° C. reverses the whole process and turns the a mating-type off and turns the MFα1 on (Herskowitz, I. & Oshima, Y. (1982) in The molecular biology of the yeast saccharomyces, (eds. Strathern, J. N., Jones, E. W. & Broach, J. R., Cold Spring Harbor Lab., Cold Spring Harbor, N.Y., pp 181–209).

The polyadenylation sequences are provided by the 3'-end sequences of any of the highly expressed genes, like ADH1, MFα1, or TPI (Alber, T. and Kawasaki, G., J. of Mol. & Appl. Genet. 1:419–434, 1982).

A number of yeast expression plasmids like YEp6, YEp13, YEp24 can be used as vectors. A gene of interest such as TPA can be fused to any of the promoters mentioned above, and then ligated to the plasmids for expression in various yeast hosts. The above-mentioned plasmids have been fully described in the literature (Botstein, et al., Gene, 8:17–24, 1979; Broach. et al., Gene, 8:121–133, 1979).

Although the above-mentioned plasmids can be and have been used to express foreign genes in yeast, disclosed herein are vectors which allow significant flexibility with respect to insertion and/or excision of various components of the expression vectors. One such example is the vector pα1-ADHt illustrated in Chart 18.

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, Nature (London), 275:104–109 (1978); and Hinnen, A., et al., Proc. Natl. Acad. Sci.— USA, 75:1929–1933 (1978). The second procedure does not involve removal of the cell wall. Instead the cells are treated with lithium-chloride or acetate and PEG and put on selective plates (Ito, H., et al., J. Bact., 153:163–168, 1983).

TPA analogs can be isolated by lysing the cells and applying standard protein isolation techniques to the lysates. TPA analogs can be detected by using Western blot techniques or radioimmunoassays.

I. EXPRESSION IN CELL CULTURES

The TPA analog encoding DNA can be ligated to various expression vectors for use in transforming host cell cultures. The vectors all contain gene sequences to initiate transcription and translation of the TPA analogs that are compatible with the host cell to be transformed. When the host cell is a higher animal cell, e.g., a mammalian cell, the naturally occurring transcription and translation gene sequence of the TPA gene can be employed or the naturally occurring gene sequence can be employed along with a heterologous promoter sequence. In addition, the vectors preferably contain a marker to provide a phenotypic trait for selection of transformed host cells. Additionally a replicating vector might contain a replicon.

Illustrative of cell cultures useful for the production of TPA analogs are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines. Illustrative insect cell lines include *Spodoptera frugiperda* (fall armyworm) and *Bombyx mori* (silkworm).

As indicated above, the vector, e.g. a plasmid, which is used to transform the host cell, preferably contains gene sequences to initiate the transcription and translation of the TPA gene sequence. These sequences are referred to as expression control sequences. When the host cell is of insect or mammalian origin illustrative useful expression control sequences are obtained from the SV-40 promoter (Science, 222, 524–527, (1983)). the CMV I.E. promoter (Proc. Nat'l. Acad. Sci., 81:659–663, 1984) or the metallothionein promoter (Nature, 296, 39–42 (1982)). As noted above, when the host cell is mammalian one may use the expression control sequences for the TPA gene but it is preferably to combine the TPA analog with a heterologous transcription initiation site. The plasmid or replicating or integrating DNA material containing the expression control sequences is cleaved using restriction enzymes and adjusted in size as necessary or desirable and ligated with cDNA coding for TPA analogs by means well known in the art.

As with yeast, when higher animal host cells are employed, polyadenylation or terminator sequences from known mammalian genes need to be incorporated into the vector. An example of a terminator sequence is the polyadenylation sequence from the bovine growth hormone gene.

Additionally, gene sequences to control replication in the host cell may be incorporated into the vector such as those found in bovine papilloma virus type-vectors. Saveria-Campo, M., "Bovine papilloma virus DNA: a eukaryotic cloning vector" in DNA Cloning Vol II a practical approach Ed. D.M. Glover, IRL Press, Arlington. Va. pages 213–238 (1985).

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, and microinjection of the DNA directly into the cells.

The transformed cells are grown up by means well known in the art, Biochemical Methods in Cell Culture and Virology, Kuchler, R. J., Dowden, Hutchinson and Ross, Inc., (1977), and the expressed TPA analogs are harvested from the cell medium in those systems where the protein is excreted from the host cell or from the cell suspension after disruption of the host cell system by, e.g., mechanical or enzymatic means which are well known in the art.

J. EVALUATION OF TPA ANALOGS

TPA and its analogs can be evaluated in either of two ways. The relative ability to cleave plasminogen into plasmin can be assessed and the relative ability of inhibitors to prevent production of plasmin can be assessed. The following details describe the procedures for such evaluations.

Amidolytic assay. The functional activity of the TPA analogs is measured by using the coupled amidolytic assay described by Verheijen, J. H., et al., A simple, sensitive spectrophotometric assay for extrinsic (tissue-type) plasminogen activator applicable to measurements in plasma. Thromb. Haemostas., 48:266–269 (1982). Briefly, samples containing the TPA analogs are mixed with plasminogen and CNBr-digested fibrinogen fragments. The plasmin thus formed then cleaves an exogenously added chromogenic substrate, S-2251 (H-D-Valyl-L-leucyl-L-lysins-p-nitroanilide dihydrochloride; KABI, Stockholm, Sweden), generating a colored product that is monitored spectrophotometrically. The effect of protease inhibitors on the activity of the TPA analogs is assessed by using a modification of this assay described by Verheijen, J. H., et al., Evidence for the occurrence of a fast-acting inhibitor for tissue-type plasminogen activator in human plasma. Thromb. Haemostas., 51:392–395 (1984). The added inhibitor binds to the TPA, forming an irreversible complex and thereby preventing the TPA from activating the plasminogen. For example, purified native TPA is titrated with increasing amounts of an inhibitor-containing sample and the residual TPA activity is measured as outlined above. A standard curve is then developed by graphically representing the residual TPA activity as a function of the amount of inhibitor-containing sample added. In like manner, the TPA analogs are titrated with the inhibitor. The resulting curves are compared to that of the TPA standard. The degree of similarity between the curves relates directly to the susceptibility of the particular analog to inhibition.

Fibrin autography. The molecular weights of the TPA analogs are estimated by subjecting samples that contain the analogs to sodium dodecyl sulfate-polyacrylamide gel electrophoresis (SDS-PAGE) and then placing the acrylamide gel onto a plasminogen-containing fibrin indicator film. As the analog proteins diffuse from the acrylamide gel into the indicator film they convert the plasminogen into plasmin, which causes the formation of a clear zone of fibrinolysis in the otherwise opaque fibrin indicator. The appearance of this zone indicates the presence of an active TPA analog at a corresponding position in the acrylamide gel. This technique also is used to assess the interaction between TPA analogs and protease inhibitors. As mentioned above, this interaction results in the formation of an enzyme-inhibitor complex, which has a higher molecular weight than the analog itself. After SDS-PAGE, the complex exhibits residual TPA activity that can be visualized in the fibrin indicator film. The details of this technique were originally described by Granelli-Piperno, A. and E. Reich, A study of proteases and protease-inhibitor complexes in biological fluids. J. Exp. Med., 148:223-234 (1978).

Assessment of the antigen of TPA analogs

Sandwich-type enzyme-linked immunosorbent assays (S-ELISAs). The antigen of TPA analogs is measured immunologically by two different S-ELISAs. The first employs goat polyclonal antibodies specific for human uterine TPA. The second uses a murine monoclonal antibody. This monoclonal antibody is specifically directed against an epitope required for the activity of TPA. The use of an antibody specific for the active-site domain of TPA provides an effective way of measuring the antigen of any TPA analog whose primary structure has been altered in a domain other than the active site. This assay is similar to one described by Korninger, C., et al., Sandwich ELISA for TPA antigen employing a monoclonal antibody. Thromb. Res., 41:527-535 (1986). The limit of sensitivity for both of the assays is approximately 1 ng of TPA per ml.

Western immunoblotting technique. The ability of the TPA analogs to form complexes with inhibitors also can be assessed by using SDS-PAGE and Western immunoblotting techniques as originally described by Towbin, H., et al., Electrophoretic transfer of proteins from polyacrylamide gels to nitrocellulose sheets: procedure and some applications. Proc. Natl. Acad. Sci. USA, 76:4350-4354 (1979). Briefly, the TPA analog is allowed to interact with the inhibitor, the mixture is subjected to SDS-PAGE, and the proteins are electrotransfered to nitrocellulose paper. Both uncomplexed, free TPA and TPA in complex with the inhibitor are detected by using purified polyclonal goat IgG specific for TPA and a rabbit antiserum directed against the goat IgG. The TPA-containing immunocomplexes are then visualized by using $I^{125}$-labeled protein A and autoradiography. cl DEFINITIONS The term "cell culture" refers to the containment of growing cells derived from either a multicellular plant or animal which allows for the cells to remain viable outside the original plant or animal.

The term "domain" refers to a discrete continuous part of an amino acid sequence that can be equated with a particular function. With respect to TPA, the above cited references have defined the domain regions and Table 5 herein discloses the approximate locations of the mid points of the interdomain regions which lie between the domains.

The term "downstream" identifies sequences proceeding farther in the direction of expression; for example, the coding region is downstream from the initiation codon.

The term "interdomain" refers to the regions of a protein's amino acid sequence that lie between the domains. In this application the interdomain regions are plus or minus five amino acid residues from the mid points illustrated in Table 5. Thus the interdomain region between the finger and growth factor domains lies between and including amino acids 44 to 55; the interdomain between the growth factor and kringle 1 domains lies between and including amino acids 86 to 97; the interdomain between kringle 1 and kringle 2 domains lies between and including amino acids 169 to 180; the interdomain between kringle 2 and the active site lies between and including amino acids 257 to 268.

The term "maintained" refers to the stable presence of a plasmid within a transformed host wherein the plasmid is present as an autonomously replicating body or as an integrated portion of the host's genome.

The term "microorganism" includes both single cellular prokaryote and eukaryote organisms such as bacteria, actinomycetes and yeast.

The phrase "non-native endonuclease restriction sites" refers to endonuclease restriction sites that are not found at the equivalent position of the native cDNA sequence. These include both unique and nonunique sites.

The term "operon" is a complete unit of gene expression and regulation, including structural genes, regulator genes, and control elements in DNA recognized by regulator gene product.

The term "plasmid" refers to an autonomous self-replicating extrachromosomal circular DNA and includes both the expression and nonexpression types. Where a recombinant microorganism or cell culture is described as hosting an expression plasmid the term "expression plasmid" includes both extrachromosomal circular DNA and DNA that has been incorporated into the host chromosome(s).

The term "promoter" is a region of DNA involved in binding the RNA polymerase to initiate transcription.

The term "DNA sequence" refers to a single or double stranded DNA molecule comprised of nucleotide bases, adenosine, thymidine, cytosine and guanosine.

The term "suitable host" refers to a cell culture or microorganism that is compatible with a recombinant plasmid and will permit the plasmid to replicate, to be incorporated into its genome or to be expressed.

The term "upstream" identifies sequences proceeding in the opposite direction from expression; for example, the bacterial promoter is upstream from the transcription unit, the initiation codon is upstream from the coding region.

Conventions used to represent plasmids and fragments in Charts 1-27, though unique to this application, are meant to be synonymous with conventional representations of plasmids and their fragments. Unlike the conventional circular figures, the single line figures on the charts represent both circular and linear double-stranded DNA with initiation or transcription occurring from left to right (5' to 3'). Asterisks (*) represent the bridging of nucleotides to complete the circular form of the plasmids. Fragments do not have asterisk marks because they are linear pieces of double-stranded DNA. Endonuclease restriction sites are indicated above the line. Gene markers are indicated below the line. Bars appearing below the diagrams representing the plasmid or fragments are used to indicate the number of basepairs between two points on the DNA. The relative spacing between markers do not indicate actual distances but are only meant to indicate their relative positions on the illustrated DNA sequence.

PREPARATIONS

Preparation 1

The Vector—pSK4—Charts 1-3

Plasmid pSK4 is an expression vector capable of directing expression of heterologous proteins in *E. coli.*

It has a strong, regulatable promoter to mediate transcription and a strong ribosome binding site for translation initiation. Specifically pSK4 uses the promoter and ribosome binding site (RBS) from the trpytophan (trp) operon. A unique ClaI site immediately downstream from the RBS is available for insertion of desirable genes such as TPA. (Chart 3).

To make plasmid pSK4, it is necessary to clone novel pTRZ1 (Chart 1) with pKC7, which is known (Chart 2). Rao, R. N. and Rogers, S. G., Gene, 7:79-82 (1979). Plasmid pTRZ1 contains a portion of the trp operon which includes the promoter/operator region, ribosome binding site, and a trpLE fusion ΔALE1413 as well as the structural genes for the galactosidase (lacZ) and lactose permease (lacY). Plasmid pKC7 is a derivative of pBR322 specifying resistance to ampicillin and kanamycin and having many unique restriction endonuclease sites.

The recombinant plasmid of pTRZ1 and pKC7 yields pSK3 having the trp promoter, RBS, and LE within pKC7. Plasmid pSK3 is then modified to eliminate the fused peptide sequence trpLE to yield the general expression vector pSK4.

(1) Construction of pTRZ1—Chart 1

Plasmid pTRZ1 is a clone of known plasmids pMC1403 and pVV1.

Plasmid pMC1403 provides the lacZ gene of pTRZ1 minus the N-terminal eight amino acids and is fully described by Casadaban, M. J., et al., J. Bacteriol, 1980, 143: 971-980. Plasmid pMC1403 has three unique restriction enzyme cleavage sites. It is cut with EcoRI, dephosphorylated with bacterial alkaline phosphatase, and the ends are made blunt with Klenow fragment of E. coli DNA polymerase I. Plasmid pVV1 provides the trp promoter and operator sequence and is fully described by Nichols, B. P. and Yanofsky, C., 1983, Methods in Enzymology, eds. L. Grossman and K. Moldave, 101: 155-164, Academic Press, N.Y. Plasmid pVV1 contains the trp operon, with a 952 base-pair deletion (ΔLE1413) fusing the trp leader sequence to the trpE gene forming trpLE. Plasmid PVV1 is cut with PvuII and BglII to yield fragment 2 (323 bp) which is isolated by preparative agarose gel electrophoresis. The BglII site is filled by Klenow enzyme. Fragment 2 is then ligated with pMC1403 to give pTRZ1.

(2) Construction of pSK3

The structural genes LacY and LacZ of pTRZ1 are unnecessary for the construction of pSK4 and their deletion will provide a smaller plasmid with more unique cloning sites. Additionally, the deletion of LacY will avoid the deleterious effects of over-production of a membrane-bound protein. As shown in Chart 2. the trp sequences (fragment 3) are excised from pTRZ1 by EcoRI/BamHI digestion, treated with alkaline phosphatase to minimize reinsertion, and then inserted into the EcoRI/BamHI region, fragment 4, of pKC7 which as a result of the digestion no longer specifies resistance to kanamycin. The clones having ampicillin resistance (AmpR) and kanamycin sensitivity (KanS) are screened for restriction fragments expected for the insertion of the trp promoter/operator sequence. This plasmid is called pSK3 and its equivalents are as described in Chart 2.

(3) Construction of pSK4

The trp promoter of pSK3 still retains the trpLER peptide which is unnecessary for the construction of a direct expression vector. The trpLE segment is excised by the following procedure. As described in Chart 3, the EcoRI/BamH fragment 5 carrying the trp sequences is cut from pSK3 and purified by electroelution from polyacrylamide gels. As shown, this fragment contains three TaqI sites, one of which is in the promoter/operator region, (TaqI") and one of which is between the ribosome binding site and the start of trpLE translation (TaqI'''). The fragment is partially digested by TaqI and the entire assortment of fragments are used in a ligation reaction with pBR322 previously cleaved with both EcoRI and ClaI.

TaqI recognizes T↓CGA (arrows denote point of strand scission) while ClaI recognizes AT↓CGAT. Since these two enzymes produce compatible cohesive ends, and the base 5' to the TaqI''' site between the ribosome binding site and trpLE is an A, (J. of Bact., 133:1457-1466) ligation of this TaqI end to the ClaI end regenerates the ClaI site. Note that this cloning scheme selects for single TaqI cuts and also ensures that transcription from the promoter will be in a clockwise direction. Clones displaying a 278 bp EcoRI/ClaI insert, and restriction patterns characteristic of the trp promoter are chosen and will be the equivalent of pSK4. The clones are useful for the expression of protein sequences capable of translation initiation when inserted at the ClaI site.

Preparation 2. Isolation of a Full Length cDNA Coding for Human Tissue Plasminogen Activator A. Materials and Methods (1) Growth of Bowes Melanoma Cells Bowes represents an established cell line derived from a human spontaneous melanoma and is a gift of Dr. Daniel Rifkin of the New York University School of Medicine. Cells are cultured in Dulbecco's Modified Eagle Medium (Gibco) supplemented with 10% fetal bovine serum (Gibco) and 50 μg/ml gentamycin (Sigma) in a humidified atmosphere at 37, using 95% air/5% $CO_2$. Cells harvested for RNA preparation are grown to confluency in Falcon 150 $cm^2$ flasks.

(2) TPA mRNA Preparation

RNA from Bowes melanoma cells is isolated essentially as described by Lizardi, et al. Anal. Biochem., vol. 98, pp. 116-122 (1979).

DNA is polyA+ enriched by passage over an oligo-deoxythymidine-cellulose (OdT-cellulose-Collaborative Research) column as described by Aviv, H. et al., Proc. Nat. Acad. Sci., vol. 69, pp. 1408-12 (1972). Typical yield from 10-150 $cm^2$ flasks twice selected on separated OdT columns is approximately 50 μg polyA+ mRNA.

The polyA+ mRNA is fractionated by centrifugation through 15-30% linear sucrose gradients. PolyA+ mRNA (~300 μg) dissolved in 200-400 μl of sterile distilled $H_2O$ is loaded onto a gradient and centrifuged in a Beckman SW41 Ti rotor at 35,000 RPM for 18 hours, 0.5 ml fractions are collected, using the Buchler Auto Densi-Flow Model IIC to harvest from top to bottom, connected to a Gilson Micro fractionator (Model FC80-K). Aliquots from each fraction are injected into Xenopus oocytes and translation products are assayed for plasminogen activator activity by the casein-agar plate method analogous to that described by Miskin, R. et al., Nuc. Acids Res. vol. 9, pp. 3355-63.

TPA activity is rendered by mRNA migrating at about 19S.

Specifically, the tissue plasminogen activator TPA is assayed by observing the conversion of plasminogen to plasmin, a non-specific protease, which digests casein. The assay is performed as follows. 0.5 ml of 8% casein, boiled, is mixed with 1 ml 2×MBS and heated to 50° C. 3% agarose is melted and cooled to 50° C. 0.5 ml of the 3% agarose is added to the casein/MBS and mixed by pipetting. 100 µl of 1 mg/ml human plasminogen is added (final concentration is 50 µg/ml) with mixing and the material is poured into a 3.5 cm diameter plastic petri dish. The agarose solution is cooled to room temperature (about 30 minutes). 2 mm diameter holes in the agarose are cut with Biorad cutter gel punches. The holes are made just before use and the wells are filled with MBS. One or two oocytes which have been injected with TPA RNA at least 6 hours prior to assay are added to each well. Incubation is in a humidified dish for 12–24 hours. Clear zones of casein hydrolysis are readily observed.

Fractions enriched for TPA mRNA are precipitated by addition of 2 volumes of ethanol and incubating on dry ice for 1 hour. Precipitates are collected by centrifugation at room temperature in an Eppendorf table-top microfuge, dissolved in sterile, distilled H$_2$O, pooled, and reprecipitated. This t-PA enriched polyA+ mRNA is used to generate cDNA for cloning.

(3) cDNA Synthesis

All of these reactions are assembled on ice.

(A) First Strand Synthesis using OdT$_{12-18}$ Primer

10 µg of enriched, polyA+selected Bowes mRNA (in µl H$_2$O) is incubated at room temperature for 10′ in the presence of 10 mM MeHgOH (Alfa) to aid in the unfolding of secondary structure. Subsequently, the following components are added; β-mercaptoethanol to 28 mM; RNasin (Biotec Inc) 1 unit/µl final reaction vol., 75 mM Tris base pH 8.3; 6 mM MgCl$_2$; 50 mM KCl; 10 µg oligodeoxythymidine (OdT$_{12-18}$Collaborative Research); 100 µCi α-=$p$-dCTP (Amersham); dGTP, dTTP, and dATP to 500 µm each; dCTP to 250 µm (all nucleotides from P. L. Biochemicals, dissolved to 20 mM in 10 mM Tris base pH 8 and neutralized with 1.0 M NaOH) and reverse transcriptase (Life Sciences Inc.) 1 unit/µg input RNA, in a final reaction volume of 50 µl. The reaction is allowed to incubate for 60 minutes at 42° C.

(B) First Strand Synthesis using Specific 15-mer oligonucleotides as Primers (see Panabieres. F. et al., Gene, vol. 19, pp. 321–6 (1982) for generally analogous procedures).

The obtaining of a complete cDNA strand coding for TPA from mRNA primed at the 3′ polyA tail is not always possible using the above procedure. By priming with a sequence upstream from the polyA tail one is more likely to obtain a sequence of 5′ TPA-coding cDNA that can be joined with an incomplete cDNA that was initiated at the polyA tail sequence.

Three pentadecamers are preferred for use as either probes or as primers for cDNA synthesis. Their sequences are:

| | 5′ | | | | 3′ | complementary to 3′ TPA positions; |
|---|---|---|---|---|---|---|
| 1. | TCA | CGG | TCG | CAT | GTT | 1759–1773 |
| 2. | GGG | GTT | TGA | GTC | TCG | 634–648 |
| 3. | CCC | ATC | AGG | ATT | CCG | 886–900 |

They are synthesized and purified by methods previously described.

Twenty-Five µg of polyA+selected RNA is incubated with 1 µg of primer (5-10-fold picomolar excess of primer to template) and 1.5 mM EDTA in 58 µl at 90° C. The mixture is allowed to equilibrate to room temperature slowly by immersion in a 5 ml water bath heated initially to 90°. After annealing the pentadecamer to the RNA template the following reagents are added: dithiothreitol (DTT) to 2 mM; RNasin to 1 unit/µl final reaction volume; 100 mM Tris base, pH 8.3; 11 mM MgCl$_2$; 50 mM KCl; 100 µCi α-$^{32}$P-dCTP; 500 µm each of dGTP, dTTP, and dATP; 250 µM dCTP; reverse transcriptase (Life Sciences, Inc.) to 1 unit/µg RNA. Incubation is at 20° C. for 3 hours at which point an equal amount of additional reverse transcriptase is added and the reaction is allowed to continue at 50° for 30 minutes. The reaction is terminated by phenol extraction and the RNA template is removed by alkaline hydrolysis as fully described in Maniatis.

(C) Synthesis of the Second Strand.

The second strand is synthesized in a reaction consisting of 40 mM KPO$_4$ (K-phosphate) pH 7.5; 6.6 mM MgCl$_2$; 1 mM DTT; 500 µm each of dGTP, dTTP. dATP; 250 µm dCTP., 100 µCi $^3$H-dCTP (Amersham) and 1 unit/µg input RNA of DNA polymerase Klenow fragment (BRL) in a final volume of 100 µl. The reaction is incubated at 15° C. for 4 hours and may be followed by monitoring the incorporation of $^3$H-dCTP. The reaction is terminated by phenol extraction, and double stranded cDNA precipitated as described above for first strand synthesis with the exception that NH$_4$Ac is added to 2.5 M (rather than NaCl to 0.3 M) for the first ethanol precipitation.

S$_1$ is used to remove hairpin structures. The S$_1$ reactions are carried out according to Maniatis Successful elimination of hairpins is determined by an increase of TCA-soluble counts. The reaction is terminated by phenol extraction omitting the precipitations. The aqueous phases are pooled and loaded directly onto sucrose gradients identical to those used for fractionation of polyA+ mRNA. Fractions are collected and assayed by dissolving 5 µl aliquots into 10 ml of Aquafluor scintillation fluid (New England Nuclear) and measuring both $^{32}$p and $^3$H. cDNA from relevant fractions are precipitated by addition of 2 volumes of ethanol and incubating on dry ice for 30 minutes. The precipitates are pelleted by centrifugation for 15′ at room temperature in an Eppendorf microfuge. Pellets are dissolved in sterile 0.3 M NaCl, pooled and reprecipitated. The precipitates are pelleted and dried.

(D) Tailing and Annealing of the cDNA to Vector DNA.

Homopolymer tracts of dCTP are enzymatically added to the 3′ termini of the cDNA molecules according to the methods described by Maniatis. Ideally, 10–30 residues of dCTP should be added to maximize cloning efficiency.

Vector DNA (prepared by digesting pBR322 to completion with PstI and adding homopolymer tracts of dGTP residues) is commercially available from New England Nuclear. The vector DNA can also be made according to the methods described by Maniatis. The procedure for annealing cDNA with vector DNA is also described by Maniatis. Briefly, tailed cDNA is mixed with vector in a 1:1 molar ratio in a 50 µl reaction containing 10 mM Tris pH 7.4; 0.4 M NaCl; 1 mM EDTA. Final DNA concentrations varied between 20–60 µg/ml. Annealing is accomplished by either; 1) following a defined regimen of incubations consisting of 65°/10'; 42°/60'; 37°/2 hours, and then room temperature for 2 hours, or 2) incubation at 65°/10, shutting off the water bath and allowing it to slowly equilibrate to room temperature overnight.

(E) Cloning and Sequence Confirmation of Full Length TPA cDNA. Charts 4–5.

The cDNA containing vectors are introduced into *E. coli* using transformation procedures already described The bacteria are screened in situ using the hybridization procedures described earlier.

The colony hybridizations described here use the pentadecamers also described above as probes. For use as a hybridization probe one µg of 15-mer is phosphorylated in a 50 µl reaction volume consisting of 70 mM Tris-base (pH 7.6), 100 mM KCl; 10 mM MgCl$_2$, 5 mM dithiothreitol, and 50 µCi µ$^{32}$P dATP (P. L. Biochemicals), and 1 U T$_4$ polynucleotide kinase (New England Biolabs). Incubation is at 37° for 60 minutes. In this fashion, the 15-mer can be labelled to specific activity of $1 \times 10^8$ cpm per µg.

Clones exhibiting complementary sequences to the probes are selected for secondary screening using PstI restriction analysis of the clones to determine if the digestion products are consistent with the PstI restriction map which can be obtained from the sequence given in Table 2 or Pennica et al., "Cloning and Expression of Human Tissue-type Plasminogen Activator cDNA in *E. coli*.", Nature, vol. 301, pp. 214–21 (20 Jan. 1983). The desirable clones will have a large portion of the 3' portion of the TPA cDNA. Digestion yields 4 fragments: the original pBR322 vector, an 1150 bp fragment, an 80 bp fragment and a 78 bp fragment. These results suggest an insert spanning about 1300 bp of the gene's 3'-end (nucleotides 1250–2550). To confirm this assumption, the clone is double digested with PstI and DdeI. The latter enzyme should cut the 1150 bp fragment into a 926 bp fragment and a 229 bp fragment while leaving the 78 or 80 bp fragments intact. The results of such a double digest will support the conclusion that the clone does in fact represent the 3'-end of the TPA gene.

As final proof, a mini-preparation of DNA is isolated from the clone and is sequenced by dideoxy chain termination. Minipreps of plasmid DNA are prepared as described in the General Methods section. Dideoxy sequencing is carried out as described in the General Methods section using Pentadecamer #1 as a primer in a 20:1 molar excess over template. The sequence data derived from this clone, designated pTPA H, is identical to sequence data presented by Pennica et al., Nature, vol. 301, pp. 214–21 (1983) for human tissue plasminogen activator (Chart 4).

From here the focus is on isolation of the 5'-end of the gene. To do this, cDNA is synthesized from twice-selected polyA+mRNA by primer extending from pentadecamer #1 rather than from OdT$_{12-18}$. The advantage afforded by this approach is twofold. First, because priming is specific for TPA, a higher percentage of the cDNA made should be represented by TPA specific sequences. Secondly, priming is some 800 bp 5' of the polyA tail, the site utilized by OdT$_{12-18}$ to prime first strand synthesis. This almost assures that the cDNA derived from this approach will include transcripts extending further 5' than pTPA H.

Transformation efficiency with this TPA-primed, cDNA is $2.5 \times 10^5$ transformants per µg of cDNA. Two banks totaling 25,000 transformants are generated. The concept of "gene-walking" is applied to purposely bias the screening. The pTPA H 5'-terminal 80 bp PstI fragment is gel isolated and used to probe 28,000 colonies derived from the primer extended banks. This specifically selects for clones extending at least as far 5' as pTPA H, and as a result of the primer extension approach, clones containing additional 5' sequences as well.

The screening by in situ hybridization yields a number of positives. The longest TPA insert is detected in secondary screening with Pst1 and Dde1. In this invention the clone, designated pTPA80-1, included an insert spanning nucleotides 550.1600 (chart 4).

The restriction data make it possible to determine fairly accurately ($+/- \sim 10\%$) the position of the 3' terminus. If priming begins at nucleotide 1759, and pTPA80-1 has a 3' terminus at position 1600, then a loss of approximately 160 basepairs occurs at some point during the cloning. The S$_1$ endonuclease is the most likely cause of the loss.

The orientation of pTPAH and pTPA80.1 are determined. Plasmids pTPAH and pTPH80.1 are cut with SacI and PvuI to yield fragments 7 (1251 bp) and 8 (5.1 kb) respectively which are gel isolated. The fragments are treated with bacterial alkaline phosphatase and ligated using T4 polymerase to yield pTPA3'cDNA (6.3 kb) having positions 550 to 2230 bases of the TPA cDNA. The new construct is verified by Pst1 digestion.

Since pTPA80-1 represents the longest TPA insert amongst the positives detected in the first primer extended banks, a second oligonucleotide complimentary to the coding sequence of amino acid residues 233–237 (nucleotides 886–900; 15-mer #2) is used to generate another cDNA library to complete the 5' end. This particular area of the gene is chosen so that should S$_1$ remove even as much as 200 bp from the 3' terminus of the transcript, sufficient overlap with pTPA3'cDNA would still exist to allow for assembly of the fragments.

The cDNA containing the 5' bases was ligated to PstI cleaved pBR322 and transformed in *E. coli* as described above. Transformation efficiency with this cDNA is on the order of $3.6 \times 10^4$ transformants/µg cDNA. Colonies from this library are screened with an oligonucleotide complimentary to coding sequence extending from nucleotides 645–660 (15-mer #3) and unambiguous positives are selected. Secondary screening is accomplished by Pst1 and BglII digestion and one clone, designated pTPA5'cDNA was shown to contain the remaining 5' sequences 1–750. Again, the effects of S$_1$ on insert length are apparent with pTPA5'cDNA. While priming is initiated at nucleotide 886, pTPA5'cDNA extends only to about nucleotide 750; our work showed a loss of about 136 bp.

With the entire TPA sequence available on two clones (pTPA3'cDNA and pTPA5'cDNA) the final task of assembly remains. The strategy is depicted in Chart 5.

Plasmid pTPA5'cDNA is cut with TaqI to yield fragment 9 (2194 bp). One TaqI site within the TPA sequence of pTPA5'cDNA (position 634) is highly enzyme resistant. Fragment 9 is cut with BglII and HgaI to yield fragment 10 (405 kb) having bases 188 to 593 of TPA cDNA representing the mature portion of the protein.

The middle portion of the TPA cDNA is obtained by first cutting pTPA3'cDNA with PuvII and EcoRI isolating fragment 11 (1748 bp). Fragment 11 is then cut with HgaI to yield fragment 12 (209 bp) containing bases 594 to 802.

To obtain the 3'portion of the cDNA, pTPA3'cDNA is digested with PvuI and the 6.3 kb fragment is isolated, treated with T4 polymerase, and partially digested with EcoRI to yield fragment 13 (1871 bp) containing bases 802 to 2230.

The ligation of the three parts of the cDNA involves the use of pKC7 which is publicly available and fully described in Rao, R. N., and Rogers, S. G., Plasmid pKC7: a vector containing ten restriction sites suitable for cloning DNA segments, Gene 7:79-82 (1979). Plasmid pKC7 is digested with BglII and SmaI and treated with bacterial alkaline phosphatase to yield fragment 14 (4.8 kb) which is gel isolated.

Fragments 10,12,13 and 14 are ligated in a single ligation pool. One noteworthy aspect of this strategy is the means by which the need for alkaline phosphatase treatment of the internal fragment is obviated.

Typically, multipiece ($\geq 4$ fragments) ligations produce the desired construction with very low efficiency due to concatemerization of the fragments. Treatment with alkaline phosphatase in the appropriate fashion minimizes this problem, resulting in a dramatic increase in efficiency of correct, multipiece assembly. In assembling the TPA fragments, we took advantage of the unique way in which the restriction endonuclease, HgaI, cuts DNA. The recognition (binding) sequence of the enzyme is GACGC but the enzyme cuts at a point beyond that recognition sequence. As a result, fragments cut with HgaI will ligate only with their originally contiguous counterpart. Self-ligation promoted by the HgaI overhang cannot happen. The 4-piece TPA ligation contains two fragments bearing an HgaI terminus. That in addition to treatment of the vector with alkaline phosphatase (to minimize self-closure) results in most of the transformants bearing the correctly assembled TPA gene. Correct assembly is verified by the restriction digests. The plasmid containing the complete cDNA sequence for TPA is designated pTPAcDNA (7.4 kb).

EXAMPLES

EXAMPLE 1

Preparation of synthetic oligonucleotides

Eighty-seven separate oligonucleotides (Table 4) were synthesized according to the procedures described earlier. The described strategy will assemble the 1084 basepairs of synthetic DNA between the BglII site at position 187 and the EcoRI site at position 1287 into pTPA-B1,2,3 (Chart 9). The specific restriction sites chosen for insertion into the interdomain regions are depicted in Charts 10 and 11. Each block is recombined with a suitable cloning vector for replication in E. coli and for verifying the sequence. All ligation and cloning methodology used is as described by Maniatis et al. supra. All cloned sequences are sequenced using the Sanger dideoxy sequencing technique to verify the sequence.

Block 1. Oligonucleotides P1-P4, P8-P11 are annealed and ligated to form a double stranded segment which is ligated to a second segment comprised of oligonucleotides P5-P7 and P12-P14. The resulting block 1 contains the sequence coding for the finger domain. Block 1 is cloned into the BglII and SphI sites of pSK4 described in Preparation 1.

Block 2. Oligonucleotides P15-P18 and P19-P23 which contain the sequence coding for the finger domain are ligated together in a single step annealing and ligation to form block 2. and cloned into the SphI and ClaI site of pBR322.

Block 3. Oligonucleotides P24-P28, P34-P38 are annealed and ligated to form a double stranded segment which is ligated to a second segment comprised of oligonucleotides P29-P33 and P39-P43. The resulting block 3 contains the sequence coding for the kringle 1 domain. Block 3 is cloned into the ClaI and BamHI sites of pBR322.

Block 4. Oligonucleotides P44-P47 and P67-P70; P48-P51 and P71-P74; P52, P53, P92, P93 and, P75, P76, P94, P95; P57-P61 and P80-P84., and P62-P66 and P85-P89 are each annealed in 5 separate tubes into double stranded segments which are then pooled and ligated to form block 4. Block 4 contains the DNA sequence coding for the kringle 2 domain. Block 4 is cloned into the BamHI and EcoRI sites of pBR322.

EXAMPLE 2

The assembly of blocks 1.4 with the active site of the TPA cDNA. Charts 6-11

The following example provides a summary of the steps needed to assemble the various synthetic blocks of Example 1 into a gene capable of encoding for a biologically active TPA. Two prototype genes are described. The plasmid pTPA-B1,2,3,4(a) has a gene encoding TPA which has no artificially-introduced endonuclease sites between the kringle 2 domain and the active site. Plasmid pTPA-B,1,2,3,4 has a gene encoding TPA which does have artificially-introduced endonuclease restriction sites between kringle 2 and the active site.

A. Construction of pTPA-B1—Chart 6

Plasmid pSK4 is digested with ClaI and SphI and the large 4.1 kb fragment 15 is isolated and ligated to the Block 1 fragment using a ClaI/XbaI linker. The ligation mixture is transformed into HB101 using the calcium chloride transformation procedure described by Maniatis. The transformants are screened with nick translated Block 1 fragments using the nick translation procedure described by Maniatis et al. Transformants hybridizing to the probe are then sequenced using the Sanger dideoxy sequencing technique to verify the correct sequence and orientation. This new transformant is denoted pTPA-B1 (4.25 kb).

B. Construction of pTPA-B1,2—Chart 7

Plasmid pTPA-B1 is digested with EcoRI and SphI and fragment 16 (450 bp) is isolated. Plasmid pBR322 is digested EcoRI and ClaI and the large fragment 17 (4.35 kb) is gel isolated. Fragments 16 and 17 are then ligated to the synthetic SphI/ClaI Block 2. The ligation mixture is transformed into HB101 and the transformants screened with nick translated Block 2. Transformants hybridizing to the probe are sequenced to confirm that they contain Block 2 in its proper orientation. This construction is designated pTPA-B 1.2 (4.8 kb).

C. Construction of pTPA-B 1,2(a)—Chart 8

Plasmid pTPA-B 1,2(a) contains HindIII and BglII restriction sites upstream from the finger and growth factor domains. Plasmid pTPA-B 1,2 is digested with XbaI and EcoRI and the large 4.5 kb fragment 18 is gel isolated and ligated to an oligonucleotide linker containing a HindIII and BglII site. The ligation mixture is transformed into HB101 and transformants screened for the presence of the HindIII/BglII sites. The new construction is designated pTPA-B 1,2(a) (4.5 kb).

D. Construction of pTPA-B 1,2,3—Chart 9

Plasmid pTPA-B 1.2(a) is digested with ClaI and BamHI and the large 4.0 kb fragment 19 is isolated. This fragment is ligated to the synthetic ClaI/BamHI kringle 1 region comprising block 3 (270 bp) and transformed into HB101. The transformants were screened with nick translated block 3. Transformants hybridizing to Block 3 were sequenced to confirm the sequence and orientation. This new construction is designated pTPA-B 1,2,3 (4.3 kb).

E. Construction of pTPA-B 1,2,3,4a—Chart 10

This plasmid contains an entire prototype TPA gene encoding for a TPA analog having enzymatic activity. There are in this gene no changes to the interdomain region between kringle 2 and the active site. Construction of pTPA-B 1,2,3,4a (4.2 kb) requires several steps. Plasmid pTPAcDNA (Chart 5) is cut with ScaI and fragment 20 (6.0 bp) encoding for the 3'end of the TPA gene is gel isolated. Plasmid pTPA-B 1,2,3 (Chart 9) is cut with ScaI and BamHI to obtain fragment 21 (1100 bp) containing the Finger, Growth Factor and kringle 1 domains. A third fragment 4a (230 bp) is obtained by cutting block 4 with BamHI and ScaI. The three fragments are ligated using T4 ligase to obtain pTPA-B 1,2,3,4a. The TPA gene is cut out of pBr322 using HindIII and AatII to yield a 2.2 kb fragment which is subcloned into pUC-19. Plasmid pUC-19 is commercially available from a variety of sources and contains a selection of restriction sites in its DNA sequence which makes TPA domain manipulation less cumbersome.

F. Construction of pTPA-B 1,2,3,4—Chart 11

This plasmid contains an entire prototype TPA gene encoding for a enzymatically active TPA analog. In this analog all 4 domains and the active site are present with unique restriction sites engineered into all the interdomain regions including the region between kringle 2 and the active site. The plasmid is constructed by first cutting pTPA-B 1,2,3,4a with EcoRI and BamHI and isolating the large 3.7 kb fragment containing the Finger, Growth Factor and kringle 1 domains. The synthetically created block 4 is obtained from its clone through a digestion with BamHI and partial digestion with EcoRI to yield intact block 4 having 560 kb. The two fragments are ligated using T4 ligase to obtain pTPA-B 1,2,3,4.

Plasmid pTPA-B 1,2,3,4a and pTPA-B 1,2,3,4 can be used to construct a variety of synthetic TPA analogs.

Example 3

Construction of TPA analogs

A. Construction of pFK1K2A (deletion of growth factor domain)

Plasmid pTPA-B 1,2,3,4a is digested with EcoRV and partially with HpaI to digest the site at 334 but not at 724. The large fragment (6.9 kb) is isolated and religated to form pFK1K2A. Plasmid pFK1K2A is then transformed into HB101 or some other suitable host. The plasmid is then screened for correct orientation and sequence.

B. Construction of pFK2A (deletion of growth factor and kringle 1 domain)

Plasmid pTPA-B 1,2,3,4 is digested with HpaI. The large 6.5 kb fragment is isolated and religated to form pFK2A. The plasmid is transformed into HB101 or some other suitable host and screened for correct orientation and sequence.

C. Construction of pFK2K2A—Chart 12 (deletion of growth factor and kringle 1 and duplication of kringle 2)

Plasmid pTPA-B 1,2,3,4 (Chart 11) is digested with HpaI to obtain fragment 22 (6.5 kb) which is isolated. A second sample of pTPA-B 1,2,3,4 is digested with HpaI and MstI and the resulting 560 bp fragment 23 containing the kringle 2 domain is isolated. The HpaI digested FK2A fragment is blunt end ligated to the HpaI/MstI fragment to yield pFK2K2A (6.5 kb). Plasmid pFK2K2A is then transformed into HB101 and screened for correct orientation and correct sequence.

D. Expression in *E. coli* Plasmid pTPAExp1—Chart 13

Expression of TPA analogs can be accomplished in *E. coli* by using the expression plasmid pTPA-B1,2 illustrated in chart 7, pTPA-B1 illustrated in Chart 6, or their equivalents. Any of the analogs can be placed within the XbaI and BamHI sites for expression. To express pFK2K2A in E. coli, nTPA-B 1,2 (Chart 7) and pFK2K2A (Chart 12) are both cut with XbaI and BamHI and fragments 24 (4.2 kb) and 25 (2.0 kb) are gel isolated. Fragments 24 and 25 are ligated to form expression plasmid pTPAExp1 (6.2 kb).

Plasmid pTPAExp1 contains a Trp promoter and operator and expression is constitutive. Culturing of *E. coli* is according to Maniatis (Supra) The *E. coli* cultures will not produce active TPA. The TPA produced by *E. coli* must be refolded into the native state. By following known cysteine reshuffling procedures one can obtain active TPA. U.S. Pat. No. 4,511,502.

EXAMPLE 4

Expression in Eukaryotes

A. Expression of Human TPA in Yeast

This example illustrates the construction of yeast expression plasmid pα1-FK2K2A having a MFα1 promotor and pre-pro sequences. Culturing conditions and preferred host strains are also provided for the expression of TPA analogs in yeast.

(1) Construction of pα1-ADHt, a Yeast Expression Vector

Plasmid, pα1-ADHt, is a multi-purpose expression vector for yeast. Restriction sites at convenient points have been engineered into its structure and control under the MFα1 promoter is generally compatible with high levels of expression. The following steps describe the construction of pα1-ADHt (Charts 14-18)

a. Construction of pYRep3'B-Chart 14

Plasmid pYRep3'B is constructed by placing the REP III and replication origin sequences of the 2μ plasmid into the SmaI site of the URA3 gene of pYIP31 to create a convenient cassette. Both plasmids, 2μ and pYIP31, are publicly available and fully described in the literature. The 2μ plasmid was fully described by J. R. Broach in Molecular Biology of the Yeast Saccharomyces cerevisiae [Life cycle and inheritance], pp.445-470 and the RepIII region is described in Cell 34:95-104 (1983) and Cell, 35:487-493 (1983). Plasmid pYIP31 was described in Gene, 18:17-24 (1979).

Plasmid pYIP31 is first cut with SmaI and treated with bacterial alkaline phosphatase to yield fragment 26 (5.4 kb) which is isolated. The 2μ plasmid of yeast is cut with PstI and XbaI, filled with Klenow and fragment 27 (1.3 kb) is isolated. Fragments 26 and 27 are ligated using T4 DNA ligase to obtain pYRep3'B (6.7 kb).

b. Construction of pADHt-Charts 15-16

Plasmid pADHt (3.86 kb) is useful because it provides useful restriction sites to assemble a yeast expression vector.

The starting plasmid for construction of pADHt is pGG400 (4.0 kb). Plasmid pGG400 is constructed from plasmids pBR322 and pML21 which are readily available to the public. J. Bacter., 126:447-453 (1976). Specifically, the gene of pBR322 coding for tetracycline resistance is replaced with a section of pML21 coding for kanamycin resistance. Plasmid pBR322 is first cut with EcoRI and PvuII and the EcoRI overhang filled in with Klenow enzyme and isolated from an agarose gel to obtain fragment 28 (2.3 kb). Plasmid pML21 is cut with PuvII to yield fragment 29 (1.7 kb) carrying the gene for resistance to kanamycin The ligation of a PuvII cut site with a filled EcoRI site will regenerate the EcoRI site after ligation. The ligation of fragments 28 and 29 yields pGG400 which is used to construct pADHt (Chart 15).

Plasmid pADHt is constructed by cutting pGG400 with PvuII and XhoI and treating with Klenow enzyme to obtain fragment 30 (3.5 kb) which is isolated. The 3' end of yeast alcohol dehydrogenase I (ADHI) is obtained from pADHBC by first cutting with HincII and BamHI, treating with T4 polymerase and isolating fragment 31 (0.36 kb). Plasmid pADHBC is publicly available and fully described in J. Biol. Chem. 257:3018-1025 (1982). Fragments 30 and 31 are ligated to obtain pADHt among others and transformed into E. coli. Those transformants carrying pADHt will have regenerated BamHI and XhoI sites in their plasmids. These transformants are selected and the authenticity of the cloned ADHI 3'-end is confirmed by restriction enzyme analysis and by sequencing (Chart 16).

c. Construction of pADHt-REPIII—Chart 17

Plasmid pADHt-REPIII (6.2 kb) is a construction of pADHt and pYRep31B in which the URA3-REPIII-ori cassette is placed into pADHt to facilitate expression and replication in yeast. Plasmid pADHt-REPIII is useful for construction of expression vectors in yeast because the EcoRI-HindIII or EcoSI-SmaI fragments can be replaced with a desired DNA fragment carrying appropriate yeast promoters or it can be used to provide a SalI-XhoI fragment carrying a replication origin, a selectable marker and the 3' end of the yeast URA3 gene.

Plasmid pADHt is modified by cutting with BamHI, filling the ends with Klenow enzyme and inserting an 8-mer SalI linker into the filled BamHI site. Plasmid pADHt (modified) is cut with SphI and the ends are filled with T4 polymerase to yield fragment 32 (3.8 kb). Plasmid pYRep31B is cut with HindIII and fragment 33 (2.4 kb) is isolated containing the 3, end of URA3 and the 2μ RepIII region which is thought to increase stability and the origin of replication. Fragments 32 and 33 are ligated and the E. coli transformants having plasmids with an orientation of the URA3 gene allowing for a clockwise transcription are screened to obtain pADHt-REPIII.

d. Construction of pα1-ADHt—Chart 18

Construction of pα1-ADHt (6.5 kb) is completed by replacing the EcoRI-HindIII fragment of pADHt-REPIII with the EcoRI-HindIII fragment from pα1 containing the promoter and pre-pro sequence of the MFα1 gene. Plasmid pα1 is fully described by A. Singh. et al., Nucleic Acid Research, 11:4049-63 (1983) and J. Kurjan. et al., Cell, 30:933-943 (1983). Plasmid pADHt-REPIII is first cut with EcoRI and HindIII to yield fragment 34 (5.3 kb) which is isolated. Plasmid pα1 is also cut with EcoRI and HindIII to yield fragment 35 (1.2 kb) which is isolated. Fragments 34 and 35 are then ligated using T4 DNA ligase to obtain pα1-ADHt.

(2) Construction of pα1-FK2K2A, Insertion of the TPA Analog cDNA into a Yeast Expression Vector—Chart 19

The preferred expression vector for the production of TPA analogs in yeast is designated pα1-FK2K2A having an MFα1 promoter. Plasmid pFK2K2A (Chart 12) is cut with BglII to yield fragment 36 (2.0 kb) which is gel isolated. Plasmid pα1-AJ)Ht is cut with HindIII and XhoI to yield fragment 37 (5.6 kb) and provides the transcription, the polyadenylation and translational sites. The system described herein will terminate downstream from the mature TPA protein and the resulting product will have a few additional amino acids of yeast origin. To terminate translation at the precise end of the TPA gene, one can provide a termination codon.

To ensure that the analog is in phase with the reading frame of the MFα pre-pro sequences, the 5'- and 3'-ends of the analogs are unchanged. The BglII site at the 5'-end can be manipulated either by inserting another linker or by a combination of Klenow (Pol I) and Mung Bean nuclease to create a HindIII site while maintaining the reading frame-in phase with the MFα1 'pre-pro' sequences. For this example the BglII site of fragment 37 is partially filled using Klenow with adenosine and guanosine. The partially filled site is then made blunt with Mung Bean nuclease and ligated to the HindIII site of pα1-ADHt. Fragments 36 and 37 (with the partially filled in end) are ligated to yield pFK2K2A (7.6 kb). Other analog TPA genes can also be inserted bluntended in the expression vector as long as the reading frame is maintained in phase with the yeast sequences.

(3) Expression of TPA Analog from the Plasmid pα1-FK2K2A in Yeast

Yeast strain YNN227 (α,ura3.52 trpl-289) are transformed with pα1-FK2K2A. The transformants are grown in glucose minimal medium (2% glucose, 0.7% yeast nitrogen base, 1% casamino acids, 40μg/ml adenine, 50μg/ml tryptophan) for 10 hours. Cells are then pelleted out by centrifugation. The cells are lysed by vortexing with glass beads. Quantities of TPA can be detected using Western Blotting techniques or radioimmunoassay or the casein enzymatic assay in agar described earlier for xenopus oocytes.

TPA can be isolated from yeast cells by first lysing the cells with 0.5 mm glass beads followed by purification on an affinity column. Standard protein purification schemes can be applied to affect further purification.

B. Expression of TPA Analogs in Chinese Hamster Ovary Cells—Charts 20-22

The following example illustrates the preferred method for expressing pFK2K2A in Chinese hamster ovary (CHO) cells. In summary there is disclosed herein, a shuttle vector pSVCOW7 which replicates in both CHO and *E. coli* cells utilizing ampicillin resistance and dihydrofolate reductase genes as markers in *E. coli* and CHO cells respectively. Plasmid pSVCOW7 also provides the polyadenylation sequence from bovine growth hormone which is necessary for expression in CHO cells. Plasmid pSVCOW7 is first cleaved and a viral promoter and the TPA analog are inserted. Transformation culture conditions and extraction procedures for TPA expressed in CHO cells are also described below.

(1) Construction of pSVCOW7—Chart 20

The starting plasmid pSV2dhfr (available from the American Type Culture Collection or prepared according to the procedure of S. Subramani, et al., "Expression of the Mouse Dihydrofolate Reductase Complementary Deoxyribonucleic Acid in Simian Virus 40", Molecular and Cellular Biology 2:854-864 (Sept. 1981) is digested with BamHI and EcoRI to yield the fragment 38 (5.0 kb) containing the ampicillin resistance gene, the SV40 origin, and the dhfr gene. The second portion of pSVCOW7 is obtained from plasmid pλGH2R2 which is digested with the same restriction endonucleases used to cleave pSV2dhfr to obtain fragment 39 containing the 3' end of genomic bovine growth hormone gene, i.e., BGH gDNA. Plasmid pλGH2R2 is publicly available from an *E. coli* HB101 host, deposited with the Northern Regional Research Laboratories in Peoria, Illinois (NRRL B-15154). Fragments 38 and 39 are ligated to yield pSVCOW7 (7.1 kb).

(2) Construction of pTPA-cDNA'BamHI—Chart 21

In order to conveniently insert a TPA analog into pSVCOW7 it is necessary to insert a convenient BamHI site within the leader sequence of TPA which is upstream from the mature protein sequence. To accomplish this pTPA5'cDNA (Chart 5) is cut with HgaI and fragment 40 (517 bp) containing bases 78 to 593 is made flush with Klenow enzyme. The flush ends are ligated to a 10-mer BamHI linker and fragment 40 is cut with NarI to yield fragment 41 having bases 68 to 521 of the TPA cDNA.

Plasmid pTPA-cDNA (Chart 5) is cut with NarI and BglII and fragment 42 (1644 bp) containing the 3, portion of the TPA cDNA is gel isolated. Fragments 41 and 42 are ligated to fragment 43 (4.3 kb) resulting from a BamHI and BglII digestion of pKC7 to yield pTPA-cDNA'BamHI (6.5 kb).

(3) Construction of pTPA-IE-PA Chart 22

Plasmid pTPA-IE-PA containing a TPA modified cDNA having the native arrangement of TPA domains is capable of being expressed by CHO cells or capable of being used to facilitate the construction of alternative expression plasmid containing TPA analogs. The assembly of pTPA-IE-PA is accomplished in two steps. First the TPA cDNA from pTPA-cDNA is inserted into pSVCOW7 and then the immediate early promoter of cytomegalovirus is inserted to initiate transcription of the TPA analog.

STEP 1. Plasmid pSVCOW7 is cut with EcoRI and PuvII and fragment 44 (600 bp) containing the polyadenylation sequence of bovine growth hormone extending from the PvuII site in the 3' most exon of the BGH gene, to the EcoRI site downstream from the 3' end. For a complete discussion of the BGH polyadenylation sequence see the following references: (1) European patent application 0112012, published on 27 June 1984 wherein the identification and characterization of bGH genomic DNA is disclosed; (2) Woychik, R. P. et al., "Requirement for the 3' Flanking Region of the Bovine Growth Hormone Gene for Accurate Polyadenylation", Proc. Natl. Acad. Sci. USA 81:3944-3948 (July 1984); and, D. R. Higgs, et al., Nature 306:398-400 (24 November 1983) and references cited therein.

A second sample of pSVCOW7 is cut with EcoRI and BamHI to yield fragment 45. Fragment 45 can be alternatively derived from the EcoRI/BamHI fragment from parent plasmid pSV2dhfr available from Bethesda Research Laboratories Fragment 45 contains the origin of replication from pBR322 and an ampicillin resistance gene expressed in *E. coli* which allows for the selection of the plasmid in *E. coli* The fragment also contains the mouse dihydrofolate reductase cDNA in a construction that allows expression in mammalian cells. Subramani, et al., Mol. Cell. Biol. 1:854-864 (1981).

The TPA cDNA is obtained from fragment 46 (1.9 kb) which is obtained from cutting pTPA-cDNA'-BamHI with BamHI and BalI. Fragment 46 contains the full coding region from tPA cDNA. The BamHI cut is in cDNA coding for the 5' untranslated sequences of the mRNA, and the BalI cut is in cDNA coding for the 3' untranslated region of the cDNA.

Fragments 44, 45 and 46 are ligated to form pTPA-PA (8.4 kb) which is a replication vector capable of shuttling between *E. coli* and CHO cells. Plasmid pTPA-PA is transformed into *E coli*.

STEP 2. In step 2. pTPA-PA is converted into expression plasmid pTPA-IE-PA by inserting the immediate early gene promoter from human cytomegalovirus (CMV I.E. promoter). The CMV I.E. promoter is obtained from the PstI digestion of the CMV genome. The restriction endonuclease cleavage maps of the region of the human cytomegalovirus genome containing the major immediate early gene (CMV I.E.) have been described in detail (Stinski, et al., J. Virol. 46:1-14, 1983; Stenberg, et al., J. Virol. 49:190-199, 1984., and, Thomsen, et al., Proc. Natl. Acad. Sci. USA, 81:659-663, 1984).

These references describe a 2.0 kilobase PstI fragment which contains amongst its sequences the promoter for the major immediate early gene. The CMV I.E. promoter can be further isolated by isolation digestion of this 2.0 kb PstI fragment with Sau3AI, whereby a desired 760 base pair fragment is obtained among the products This 7αbasepair fragment can be distinguished from the other products by its size and the presence of a SacI cleavage site and a BalI cleavage site within the fragment. Because of its convenient identification, utilization of this Sau3AI fragment is the preferred method of using the CMV I.E. promoter as described in the present specification.

Plasmid pTPA-PA, constructed in Step 1, is cleaved with BamHI, and a Sau3AI fragment containing the CMV immediate early promoter is ligated into the BamHI site. Plasmids containing the CMV promoter fragment in an orientation such that transcription from the promoter would synthesize an mRNA for TPA are identified by cleavage of the plasmids with SacI. The resulting plasmid is designated pTPA-IE-PA having the CMV I.E. promoter at the 5'-end of the TPA cDNA and the bGH polyadenylation signal on its 3'-end.

(4) Construction of pTPA-IE-FK2K2A—Chart 23

The construction of pTPA-IE-FK2K2A is a two step process. Step one involves the creation of pTPA-FK2K2A which contains the desired TPA analog, the polyadenylation signal sequence from BGH and the selectable markers and replicons of pSVCOW7 and Step 2 involves the insertion of the CMV I.E. promoter discussed earlier. While the example below describes the insertion of TPA. analog FK2K2A, other analogs can be inserted using the same enzymes and procedures.

Step 1. Plasmid pTPA-IE-PA (Chart 22) is cut with BamHI and BglII to yield fragment 47 containing the TPA leader sequence bases 1-188 The polyadenylation signal sequence of BGH is obtained by cutting pSVCOW7 (Chart 20) with EcoRI and PvuII to yield fragment 48 (600 bp). The TPA analog sequence is obtained from cutting pFK2K2A (chart 12) with BglII and BalI to obtain fragment 49 (2.0 kb). A second sample of pSVCOW7 is cut with EcoRI and BamHI to yield fragment 50 (5.8 kb) containing the markers and replicons of pSVCOW7. The four fragments are gel isolated and ligated using T4 ligase to yield pTPA-FK2K2A (8.3 kb).

Step 2. Plasmid pTPA-FK2K2A is cut with BamHI and the Sau3A digested CMV-IE promoter sequence is inserted to form pTPA-IE-FK2K2A which is maintained in *E. coli* until transfection into CHO cells.

(5) Transfection and Culturing of CHO Cells

Plasmid pTPA-IE-FK2K2A is transfected into Chinese hamster ovary (CHO) cells deficient in dihydrofolate reductase(dhfr) using the calcium phosphate method for transfection of DNA into cells which is described in detail by Graham. et al. (in Introduction of Macromolecules into Viable Mammalian Cells, Alan R. Liss Inc., N.Y., 1980, pp. 3-25). The cell line used is the mutant DXB-11 originally available from L. Chasin, of Columbia University and completely described in Proc. Natl. Acad. Sci. USA 77:4216-4220, 1980). The above methods for transfection relies on the fact that cells which incorporate the transfected plasmids are no longer dhfr deficient and will grow in Dulbecco's modified Eagle's medium plus proline.

From the cells transfected with pTPA-IE-FK2K2A, clones are isolated, which, when grown in a monolayer for two days, synthesize at least 10 ng TPA per million cells. From cells with pIETPA-IPA-dhfr, clones are isolated which synthesize at least 100 ng TPA per million cells. Expression of TPA analog can be detected by radioimmunoassay, or Western blot techniques.

TPA analogs are purified according to the procedure of Rijken and Collen. Journal of Biological Chemistry 256:7035-7041 (1979). The CHO cells containing the recombinant TPA analogs are grown in serum free media. The culture media is harvested after 72 hours and applied to a zinc-chelate agarose column equilibrated with 0.02 M Tris-HCl pH 7.5 containing 1.0M NaCl and 0.01% Tween 80. The column is washed with the same buffer and the TPA analogs eluted with a linear gradient from 0 to 0.05 M imidazole in the same buffer. The fractions containing TPA analogs are pooled and applied to a concanavalin A-agarose column equilibrated with 0.01 M phosphate buffer pH 7.5 containing 1.0M NaCl and 0.01% Tween 80. After washing the column with the same buffer, the TPA analogs are eluted with a linear gradient of the equilibration buffer to 0.01 M phosphate buffer pH 7.5 containing 0.01% Tween 80, 0.4 M D-methylmannoside and 2 M potassium thiocyanate. The fractions containing TPA activity are pooled and solid KSCN is added to increase the KSCN concentration to 1.6 M. The fractions are concentrated approximately 10-fold and applied to a Sephadex G-150 column equilibrated with 0.01 M phosphate buffer pH 7.5 containing 1.6 M KSCN and 0.01% Tween 80. The fractions containing the TPA activity are pooled, dialyzed against 0.15 M NaCl and 0.01% Tween 80 and stored at −80° C.

C. Expression in *Spodoptera frugiperda*

The following example relates to the expression of TPA in insect cell cultures. All procedures are detailed in Summers, M. D. and Smith, G. E., A Manual for Baculovirus Vectors and Insect Cell Culture Procedures published by the College of Agriculture, Texas Agricultural Experiment Station, Texas Agricultural Extension Service, College Station, Texas, 1986. The starting plasmid pAc373 (7.1 kb) is a general baculovirus expression vector having a unique BamHI site immediately downstream from the polyhedron promoter for Autographa californica nuclear polyhedrosis virus (AcNPV). The polyhedron protein is a matrix protein that is nonessential for viral infection and replication in vitro. The plasmid is available from Professor Max Summers of the Department of Entomology, Texas A&M University, College Station, Tex. 77843 and is fully described in Molecular and Cell. Biology, 3(12):2156-2165 (1983).

(1) Construction of pAcTPA—Chart 24

Starting plasmid pAc373 is modified to accept the TPA analogs by inserting into the unique BamHI site a BglII site which is also unique. Plasmid pAc373 is first cut with BamHI and then treated with Mung bean nuclease to create blunt ends. BglII linkers are then ligated to the ends and the ends rejoined to yield pAc373'BglII. Plasmid pTPAcDNA'BamHI from chart 21 is fully digested with BamHI and partially digested with BglII to yield fragment 51 (1.95 Kb) coding for an intact TPA cDNA. Fragment 51 is gel isolated and inserted into the BglII site of pAc373,BglII to yield pAcTPA which is capable of expressing native TPA in *S. frugiperda*.

(2) Construction of pAcFK2K2A—Chart 25

For this expression plasmid the TPA analog FK2K2A is cut from pFK2K2A (Chart 12) using BglII and the cDNA encoding the TPA analog is gel isolated as fragment 53 (2.0 kb). Plasmid pAcTPA (Chart 24) is cut with BglII to yield fragment 52 (7.15 1:b). Fragments 52 and 53 are ligated to yield pAcFK2K2A (9.15 kb) which is maintained in E. coli until transfected into S. frugiperda.

(3) Transfection and culturing of S. frugiperda

The TPA analogs are recombined with native ACNPV DNA by co-transfection in S. frugiperda. S. frugiperda (SF9; ATCC CRL 1711) are cultured in Grace Media (Gibco Lab. Livonia, MI 48150), 10% fetal calf serum and supplemented with Difco Lactalbumin hydrolysate and yeastolate. The cells are cotransfected with AcNPV DNA and pAcTPAFK2K2A at 1μ/ml and 2μ/ml respectively. Resulting virus particles are obtained by collecting the media and removing cellular material by low speed centrifugation. The virus containing-media is then used to infect S. frugiperda. Subsequent infection of S. frugiperda using these viral particles which include both native viral DNA and DNA recombined with the cDNA coding for the FK2K2A TPA analog will result in some cells expressing the TPA analog instead of the polyhedron protein. Detection of infected cell colonies producing TPA analogs is determined by infecting a monolayer of S. frugiperda* for one hour with serial dilutions of the viral containing media ($10^{-1}-10^{-6}$). The cells are then overlayed with Grace media with 0.7% low melting point agar containing 6 mg/ml fibrinogen and 0.5 units of thrombin. Those cells producing active TPA will form clear plaques around the foci of infection.

EXAMPLE 5

The following analogs have been isolated from CHO cells and evaluated for activity and antigenicity: FGK1K2A, FK1K2A and FK2A.

Table 1 summarizes the results of two different in vitro tests, activity and antibody recognition. Analogs FGK1K2A and FK2A form complexes with a plasminogen activator inhibitor from platelets (thrombin-induced platelet releasate). The molecular weight of the analogs are about 62,000 and 40,000 daltons, respectively. The molecular weights of the enzyme inhibitor complexes are approximately 110,000 and 85,000 daltons, respectively.

EXAMPLE 6

Therapeutic application of TPA analogs

TPA is known to be therapeutically useful for dissolving thrombi. The Lancet, pp. 1018–20 (Nov. 7, 1981); Science, 220:1181 (1983)., and N. Eng. J. Med., 310:609 (1984). Administration of TPA analogs to patients with coronary thrombi can be via intracoronary or intravenous routes according to the general procedures described in the above two references.

TABLE 1

| Sample | Activity* (U/ml) | Antigen** (ng/ml) |
|---|---|---|
| Purified Native | 49,000 | 912,000 |
| Recombinant TPA | | |
| FGK1K2P | 2.1 ± .03 | 47 ± 2 |
| FK1K2P | 8.4 ± .34 | 200 ± 6 |
| FK2P | 4.2 ± .06 | 97 ± 28 |

*Activity is expressed relative to a standard TPA preparation.
**Antigen measurements were obtained using the goat polyclonal antibody to TPA described above.

TABLE 2

```
1     TTCTGAGCACAGGGCTGGAGAGAAAACCTCTGCGAGGAAAGGGAAGGAGCAAGCCGTGAA
      ||||||||||||||||||||||||||||||||||||||||||||||||||||||||||||
1     TTCTGAGCACAGGGCTGGAGAGAAAACCTCTGCGAGGAAAGGGAAGGAGCAAGCCGTGAA

61    TTTAAGGGACGCTGTGAAGCAATCATGGATGCAATGAAGAGAGGGCTCTGCTGTGTGCTG
      ||||||||||||||||||||||||||||||||||||||||||||||||||||||||||||
61    TTTAAGGGACGCTGTGAAGCAATCATGGATGCAATGAAGAGAGGGCTCTGCTGTGTGCTG

121   CTGCTGTGTGGAGCAGTCTTCGTTTCGCCCAGCCAGGAAATCCATGCCCGATTCAGAAGA
      ||||||||||||||||||||||||||||||||||||||||||||||||||||||||||||
121   CTGCTGTGTGGAGCAGTCTTCGTTTCGCCCAGCCAGGAAATCCATGCCCGATTCAGAAGA

181   GGAGCCAGATCT   TACCAAGTGATCTGCAGAGATGAAAAAACGCAGATGATATACCAG
      ||||||||||||   |||||||||||||||||||||||||||||||||||||||||||||
181   GGAGCCAGATCTAGATACCAAGTGATCTGCAGAGATGAAAAAACGCAGATGATATACCAG

238   CAACATCAGTCATGGCTGCGCCCTGTGCTCAGAAGCAACCGGGTGGAATATTGCTGGTGC
      ||||||||||||||||||||||||||||||||||||||||||||||||||||||||||||
241   CAACATCAGTCATGGCTGCGCCCTGTGCTCAGAAGCAACCGGGTGGAATATTGCTGGTGC

298   AACAGTGGCAGGGCACAGTGCCACTCAGTGCCTGTCAAAAGTTGCAGCGAGCCAAGGTGT
      ||||||||||||||||||||||||||||||||||| ||    ||||||||||||||||||
301   AACAGTGGCAGGGCACAGTGCCACTCAGTGCCTGTTAACGCATGCAGCGAGCCAAGGTGT

358   TTCAACGGGGGCACCTGCCAGCAGGCCCTGTACTTCTCAGATTTCGTGTGCCAGTGCCCC
      ||||||||||||||||||||||||||||||||||||||||||||||||||||||||||||
361   TTCAACGGGGGCACCTGCCAGCAGGCCCTGTACTTCTCAGATTTCGTGTGCCAGTGCCCC
```

TABLE 2-continued

```
418  GAAGGATTTGCTGGGAAGTGCTGTGAAATAGATACCAGGGCCACGTGCTACGAGGACCAG
     ||||||||||||||||||||||||||| || |||||| ||||||||||||||||||||||
421  GAAGGATTTGCTGGGAAGTGCTGTGATATCGATACCCGGGCCACGTGCTACGAGGACCAG

478  GGCATCAGCTACAGGGGCACGTGGAGCACAGCGGAGAGTGGCGCCGAGTGCACCAACTGG
     ||||||||||||||||||||||||||||||||||||||||||||||||||||||||||||
481  GGCATCAGCTACAGGGGCACGTGGAGCACAGCGGAGAGTGGCGCCGAGTGCACCAACTGG

538  AACAGCAGCGCGTTGGCCCAGAAGCCCTACAGCGGGCGGAGGCCAGACGCCATCAGGCTG
     ||||||||||||||||||||||||||||||||||||||||||||||||||||||||||||
541  AACAGCAGCGCGTTGGCCCAGAAGCCCTACAGCGGGCGGAGGCCAGACGCCATCAGGCTG

598  GGCCTGGGGAACCACAACTACTGCAGAAACCCAGATCGAGACTCAAAGCCCTGGTGCTAC
     ||||||||||||||||||||||||||||||||||||||||||||||||||||||||||||
601  GGCCTGGGGAACCACAACTACTGCAGAAACCCAGATCGAGACTCAAAGCCCTGGTGCTAC

658  GTCTTTAAGGCGGGGAAGTACAGCTCAGAGTTCTGCAGCACCCCTGCCTGCTCTGAGGGA
     ||||||||||||||||||||||||||||||||||||||||||||||||||||||||||||
661  GTCTTTAAGGCGGGGAAGTACAGCTCAGAGTTCTGCAGCACCCCTGCCTGCTCTGAGGGA

718  AAC    AGTGACTGCTACTTTGGGAATGGGTCAGCCTACCGTGGCACGCACAGCCTCACC
     |  |   |||||||||||||||||||||||||||||||||||||||||||||||||||||
721  TCCGTTAACGACTGCTACTTTGGGAATGGGTCAGCCTACCGTGGCACGCACAGCCTCACC

775  GAGTCGGGTGCCTCCTGCCTCCCGTGGAATTCCATGATCCTGATAGGCAAGGTTTACACA
     ||||||||||||||||||||||||||||||||||||||||||||||||||||||||||||
781  GAGTCGGGTGCCTCCTGCCTCCCGTGGAATTCCATGATCCTGATAGGCAAGGTTTACACA

835  GCACAGAACCCCAGTGCCCAGGCACTGGGCCTGGGCAAACATAATTACTGCCGGAATCCT
     ||||||||||||||||||||||||||||||||||||||||||||||||||||||||||||
841  GCACAGAACCCCAGTGCCCAGGCACTGGGCCTGGGCAAACATAATTACTGCCGGAATCCT

895  GATGGGGATGCCAAGCCCTGGTGCCACGTGCTGAAGAACCGCAGGCTGACGTGGGAGTAC
     ||||||||||||||||||||||||||||||||||||||||||||||||||||||||||||
901  GATGGGGATGCCAAGCCCTGGTGCCACGTGCTGAAGAACCGCAGGCTGACGTGGGAGTAC

955  TGTGATGTGCCCTCCTGCT CCACC    TGCGGCCT GAGACAGTACAGCCAGCCTCAGTTT
     |||||||||||||||||| | |||    |||||||||||   |||||||||||||||||
961  TGTGATGTGCCCTCCTGCGCAACCGCATGCGGCCGGAGA    TACAGCCAGCCTCAGTTT

1012 CGCATCAAAGGAGGGCTCTTCGCCGACATCGCCTCCCACCCCTGGCAGGCTGCCATCTTT
     ||||||||||||||||||||||||||||||||||||||||||||||||||||||||||||
1021 CGCATCAAAGGAGGGCTCTTCGCCGACATCGCCTCCCACCCCTGGCAGGCTGCCATCTTT

1072 GCCAAGCACAGGAGGTCGCCCGGAGAGCGGTTCCTGTGCGGGGGCATACTCATCAGCTCC
     ||||||||||||||||||||||||||||||||||||||||||||||||||||||||||||
1081 GCCAAGCACAGGAGGTCGCCCGGAGAGCGGTTCCTGTGCGGGGGCATACTCATCAGCTCC

1132 TGCTGGATTCTCTCTGCCGCCCACTGCTTCCAGGAGAGGTTTCCGCCCCACCACCTGACG
     ||||||||||||||||||||||||||||||||||||||||||||||||||||||||||||
1141 TGCTGGATTCTCTCTGCCGCCCACTGCTTCCAGGAGAGGTTTCCGCCCCACCACCTGACG

1192 GTGATCTTGGGCAGAACATACCGGGTGGTCCCTGGCGAGGAGGAGCAGAAATTTGAAGTC
     ||||||||||||||||||||||||||||||||||||||||||||||||||||||||||||
```

TABLE 2-continued

```
1201 GTGATCTTGGGCAGAACATACCGGGTGGTCCCTGGCGAGGAGGAGCAGAAATTTGAAGTC

1252 GAAAAATACATTGTCCATAAGGAATTCGATGATGACACTTACGACAATGACATTGCGCTG
     ||||||||||||||||||||||||||||||||||||||||||||||||||||||||||||
1261 GAAAAATACATTGTCCATAAGGAATTCGATGATGACACTTACGACAATGACATTGCGCTG

1312 CTGCAGCTGAAATCGATTCGTCCCGCTGTGCCCAGGAGAGCAGCGTGGTCCGCACTGTG
     |||||||||||||||||||||||||||||||||||||||||||||||||||||||||||
1321 CTGCAGCTGAAATCGATTCGTCCCGCTGTGCCCAGGAGAGCAGCGTGGTCCGCACTGTG

1372 TGCCTTCCCCCGGCGGACCTGCAGCTGCCGGACTGGACGGAGTGTGAGCTCTCCGGCTAC
     ||||||||||||||||||||||||||||||||||||||||||||||||||||||||||||
1381 TGCCTTCCCCCGGCGGACCTGCAGCTGCCGGACTGGACGGAGTGTGAGCTCTCCGGCTAC

1432 GGCAAGCATGAGGCCTTGTCTCCTTTCTATTCGGAGCGGCTGAAGGAGGCTCATGTCAGA
     ||||||||||||||||||||||||||||||||||||||||||||||||||||||||||||
1441 GGCAAGCATGAGGCCTTGTCTCCTTTCTATTCGGAGCGGCTGAAGGAGGCTCATGTCAGA

1492 CTGTACCCATCCAGCCGCTGCACATCACAACATTTACTTAACAGAACAGTCACCGACAAC
     ||||||||||||||||||||||||||||||||||||||||||||||||||||||||||||
1501 CTGTACCCATCCAGCCGCTGCACATCACAACATTTACTTAACAGAACAGTCACCGACAAC
```

```
1552 ATGCTGTGTGCTGGAGACACTCGGAGCGGCGGGCCCCAGGCAAACTTGCACGACGCCTGC
     ||||||||||||||||||||||||||||||||||||||||||||||||||||||||||||
1561 ATGCTGTGTGCTGGAGACACTCGGAGCGGCGGGCCCCAGGCAAACTTGCACGACGCCTGC

1612 CAGGGCGATTCGGGAGGCCCCCTGGTGTGTCTGAACGATGGCCGCATGACTTTGGTGGGC
     ||||||||||||||||||||||||||||||||||||||||||||||||||||||||||||
1621 CAGGGCGATTCGGGAGGCCCCCTGGTGTGTCTGAACGATGGCCGCATGACTTTGGTGGGC

1672 ATCATCAGCTGGGGCCTGGGCTGTGGACAGAAGGATGTCCCGGGTGTGTACACAAAGGTT
     ||||||||||||||||||||||||||||||||||||||||||||||||||||||||||||
1681 ATCATCAGCTGGGGCCTGGGCTGTGGACAGAAGGATGTCCCGGGTGTGTACACAAAGGTT

1732 ACCAACTACCTAGACTGGATTCGTGACAACATGCGACCGTGACCAGGAACACCCGACTCC
     ||||||||||||||||||||||||||||||||||||||||||||||||||||||||||||
1741 ACCAACTACCTAGACTGGATTCGTGACAACATGCGACCGTGACCAGGAACACCCGACTCC

1792 TCAAAAGCAAATGAGATCCCGCCTCTTCTTCTTCAGAAGACACTGCAAAGGCGCAGTGCT
     ||||||||||||||||||||||||||||||||||||||||||||||||||||||||||||
1801 TCAAAAGCAAATGAGATCCCGCCTCTTCTTCTTCAGAAGACACTGCAAAGGCGCAGTGCT

1852 TCTCTACAGACTTCTCCAGACCCACCACACCGCAGAAGCGGGACGAGACCCTACAGGAGA
     ||||||||||||||||||||||||||||||||||||||||||||||||||||||||||||
1861 TCTCTACAGACTTCTCCAGACCCACCACACCGCAGAAGCGGGACGAGACCCTACAGGAGA

1912 GGGAAGAGTGCATTTTCCCAGATACTTCCCATTTTGGAAGTTTTCAGGACTTGGTCTGAT
     ||||||||||||||||||||||||||||||||||||||||||||||||||||||||||||
1921 GGGAAGAGTGCATTTTCCCAGATACTTCCCATTTTGGAAGTTTTCAGGACTTGGTCTGAT

1972 TTCAGGATACTCTGTCAGATGGGAAGACATGAATGCACACTAGCCTCTCCAGGAATGCCT
     ||||||||||||||||||||||||||||||||||||||||||||||||||||||||||||
1981 TTCAGGATACTCTGTCAGATGGGAAGACATGAATGCACACTAGCCTCTCCAGGAATGCCT
```

-continued

```
2032 CCTCCCTGGGCAGAAGTGGCCATGCCACCCTGTTTTCGCTAAAGCCCAACCTCCTGACCT
     ||||||||||||||||||||||||||||||||||||||||||||||||||||||||||||
2041 CCTCCCTGGGCAGAAGTGGCCATGCCACCCTGTTTTCGCTAAAGCCCAACCTCCTGACCT

2092 GTCACCGTGAGCAGCTTTGGAAACAGGACCACAAAAATGAAAGCATGTCTCAATAGTAAA
     ||||||||||||||||||||||||||||||||||||||||||||||||||||||||||||
2101 GTCACCGTGAGCAGCTTTGGAAACAGGACCACAAAAATGAAAGCATGTCTCAATAGTAAA

2152 AGAAACAAGAGATCTTTCAGGAAAGACGGATTGCATTAGAAATAGACAGTATATTTATAG
     ||||||||||||||||||||||||||||||||||||||||||||||||||||||||||||
2161 AGAAACAAGAGATCTTTCAGGAAAGACGGATTGCATTAGAAATAGACAGTATATTTATAG

2212 TCACAAGGGCCCAGCAGGGCTCAAAGTTGGGGCAGGCTGGCTGGCCCGTCATGTTCCTCA
     ||||||||||||||||||||||||||||||||||||||||||||||||||||||||||||
2221 TCACAAGGGCCCAGCAGGGCTCAAAGTTGGGGCAGGCTGGCTGGCCCGTCATGTTCCTCA

2272 AAAGCGCCCTTGACGTCAAGTCTCCTTCCCCTTTCCCCACTCCCTGGCTCTCAGAAGGTA
     ||||||||||||||||||||||||||||||||||||||||||||||||||||||||||||
2821 AAAGCGCCCTTGACGTCAAGTCTCCTTCCCCTTTCCCCACTCCCTGGCTCTCAGAAGGTA

2332 TTCCTTTTGAGTACAGTGTGTAAAGTGTAAATCCTTTTTCTTTATAAACTTTAGAGTAGC
     ||||||||||||||||||||||||||||||||||||||||||||||||||||||||||||
2341 TTCCTTTTGAGTACAGTGTGTAAAGTGTAAATCCTTTTTCTTTATAAACTTTAGAGTAGC

2392 ATGAGAGAATTGTATCATTTGAACAACTAGGCTTCAGCATATTTATAGCGATCCATCGTT
     ||||||||||||||||||||||||||||||||||||||||||||||||||||||||||||
2401 ATGAGAGAATTGTATCATTTGAACAACTAGGCTTCAGCATATTTATAGCGATCCATCGTT

2452 AGTTTTTACTTTCCGTTGCCACAACCCTGTTTTATACCGTACTTAATAAATTCGGATATA
     ||||||||||||||||||||||||||||||||||||||||||||||||||||||||||||
2461 AGTTTTTACTTTCCGTTGCCACAACCCTGTTTTATACCGTACTTAATAAATTCGGATATA

2512 TTTTTTCACAGTTTTTTCCAAAAAAAAAAAAAA
     |||||||||||||||||||||||||||||||||
2521 TTTTTTCACAGTTTTTTCCAAAAAAAAAAAAAA
```
Matches = 2526
Mismatches = 15
Unmatched = 12
Lenght = 2553
Matches/length = 99.0 percent

TABLE 3

```
1   MetAspAlaMetLysArgGlyLeuCysCysValLeuLeuLeuCysGlyAlaValPheVal
    | | | | | | | | | | | | | | | | | | | |
    MetAspAlaMetLysArgGlyLeuCysCysValLeuLeuLeuCysGlyAlaValPheVal

21  SerProSerGlnGluIleHisAlaArgPheArgArgGlyAlaArgSer   TyrGlnVal
    | | | | | | | | | | | | | | | | |   | | |
21  SerProSerGlnGluIleHisAlaArgPheArgArgGlyAlaArgSerArgTyrGlnVal

40  IleCysArgAspGluLysThrGlnMetIleTyrGlnGlnHisGlnSerTrpLeuArgPro
    | | | | | | | | | | | | | | | | | | | |
41  IleCysArgAspGluLysThrGlnMetIleTyrGlnGlnHisGlnSerTrpLeuArgPro

60  ValLeuArgSerAsnArgValGluTyrCysTrpCysAsnSerGlyArgAlaGlnCysHis
    | | | | | | | | | | | | | | | | | | | |
61  ValLeuArgSerAsnArgValGluTyrCysTrpCysAsnSerGlyArgAlaGlnCysHis
```

TABLE 3-continued

```
 80  SerValProValLysSerCysSerGluProArgCysPheAsnGlyGlyThrCysGlnGln
     | | | |     | | | | | | | | | | | | | | |
 81  SerValProValAsnAlaCysSerGluProArgCysPheAsnGlyGlyThrCysGlnGln

100  AlaLeuTyrPheSerAspPheValCysGlnCysProGluGlyPheAlaGlyLysCysCys
     | | | | | | | | | | | | | | | | | | | |
101  AlaLeuTyrPheSerAspPheValCysGlnCysProGluGlyPheAlaGlyLysCysCys

120  GlyIleAspThrArgAlaThrCysTyrGluAspGlnGlyIleSerTyrArgGlyThrTrp
     | | | | | | | | | | | | | | | | | | | |
121  AspIleAspThrArgAlaThrCysTyrGluAspGlnGlyIleSerTyrArgGlyThrTrp

140  SerThrAlaGluSerGlyAlaGluCysThrAsnTrpAsnSerSerAlaLeuAlaGlnLys
     | | | | | | | | | | | | | | | | | | | |
141  SerThrAlaGluSerGlyAlaGluCysThrAsnTrpAsnSerSerAlaLeuAlaGlnLys

160  ProTyrSerGlyArgArgProAspAlaIleArgLeuGlyLeuGlyAsnHisAsnTyrCys
     | | | | | | | | | | | | | | | | | | | |
161  ProTyrSerGlyArgArgProAspAlaIleArgLeuGlyLeuGlyAsnHisAsnTyrCys

180  ArgAsnProAspArgAspSerLysProTrpCysTyrValPheLysAlaGlyLysTyrSer
     | | | | | | | | | | | | | | | | | | | |
181  ArgAsnProAspArgAspSerLysProTrpCysTyrValPheLysAlaGlyLysTyrSer

200  SerGluPheCysSerThrProAlaCysSerGluGly    AsnSerAspCysTyrPheGly
     | | | | | | | | | |                     | | | | |
201  SerGluPheCysSerThrProAlaCysSerGluGlySerValAsnAspCysTyrPheGly

219  AsnGlySerAlaTyrArgGlyThrHisSerLeuThrGluSerGlyAlaSerCysLeuPro
     | | | | | | | | | | | | | | | | | | | |
222  AsnGlySerAlaTyrArgGlyThrHisSerLeuThrGluSerGlyAlaSerCysLeuPro

239  TrpAsnSerMetIleLeuIleGlyLysValTyrThrAlaGlnAsnProSerAlaGlnAla
     | | | | | | | | | | | | | | | | | | | |
241  TrpAsnSerMetIleLeuIleGlyLysValTyrThrAlaGlnAsnProSerAlaGlnAla

259  LeuGlyLeuGlyLysHisAsnTyrCysArgAsnProAspGlyAspAlaLysProTrpCys
     | | | | | | | | | | | | | | | | | | | |
261  LeuGlyLeuGlyLysHisAsnTyrCysArgAsnProAspGlyAspAlaLysProTrpCys

279  HisValLeuLysAsnArgArgLeuThrTrpGluTyrCysAspValProSerCysSerThr
     | | | | | | | | | | | | | | | | | | |
281  HisValLeuLysAsnArgArgLeuThrTrpGluTyrCysAspValProSerCysAlaThr

299     CysGlyLeuArgGlnTyrSerGlnProGlnPheArgIleLysGlyGlyLeuPheAla
        | | | |     | | | | | | | | | | | | | |
301  AlaCysGlyArgArg   TyrSerGlnProGlnPheArgIleLysGlyGlyLeuPheAla

318  AspIleAlaSerHisProTrpGlnAlaAlaIlePheAlaLysHisArgArgSerProGly
     | | | | | | | | | | | | | | | | | | | |
321  AspIleAlaSerHisProTrpGlnAlaAlaIlePheAlaLysHisArgArgSerProGly

338  GluArgPheLeuCysGlyGlyIleLeuIleSerSerCysTrpIleLeuSerAlaAlaHis
```

TABLE 3-continued

```
         | | | | | | | | | | | | | | | | | |
341  GluArgPheLeuCysGlyGlyIleLeuIleSerSerCysTrpIleLeuSerAlaAlaHis

358  CysPheGlnGluArgPheProProHisHisLeuThrValIleLeuGlyArgThrTyrArg
         | | | | | | | | | | | | | | | | | |
361  CysPheGlnGluArgPheProProHisHisLeuThrValIleLeuGlyArgThrTyrArg

378  ValValProGlyGluGluGluGlnLysPheGluValGluLysTyrIleValHisLysGlu
         | | | | | | | | | | | | | | | | | |
381  ValValProGlyGluGluGluGlnLysPheGluValGluLysTyrIleValHisLysGlu

398  PheAspAspAspThrTyrAspAsnAspIleAlaLeuLeuGlnLeuLysSerAspSerSer
         | | | | | | | | | | | | | | | | | |
401  PheAspAspAspThrTyrAspAsnAspIleAlaLeuLeuGlnLeuLysSerAspSerSer

418  ArgCysAlaGlnGluSerSerValValArgThrValCysLeuProProAlaAspLeuGln
         | | | | | | | | | | | | | | | | | |
421  ArgCysAlaGlnGluSerSerValValArgThrValCysLeuProProAlaAspLeuGln

438  LeuProAspTrpThrGluCysGluLeuSerGlyTyrGlyLysHisGluAlaLeuSerPro
         | | | | | | | | | | | | | | | | | |
441  LeuProAspTrpThrGluCysGluLeuSerGlyTyrGlyLysHisGluAlaLeuSerPro

458  PheTyrSerGluArgLeuLysGluAlaHisValArgLeuTyrProSerSerArgCysThr
         | | | | | | | | | | | | | | | | | |
461  PheTyrSerGluArgLeuLysGluAlaHisValArgLeuTyrProSerSerArgCysThr

478  SerGlnHisLeuLeuAsnArgThrValThrAspAsnMetLeuCysAlaGlyAspThrArg
         | | | | | | | | | | | | | | | | | |
481  SerGlnHisLeuLeuAsnArgThrValThrAspAsnMetLeuCysAlaGlyAspThrArg

498  SerGlyGlyProGlnAlaAsnLeuHisAspAlaCysGlnGlyAspSerGlyGlyProLeu
         | | | | | | | | | | | | | | | | | |
501  SerGlyGlyProGlnAlaAsnLeuHisAspAlaCysGlnGlyAspSerGlyGlyProLeu

518  ValCysLeuAsnAspGlyArgMetThrLeuValGlyIleIleSerTrpGlyLeuGlyCys
         | | | | | | | | | | | | | | | | | |
521  ValCysLeuAsnAspGlyArgMetThrLeuValGlyIleIleSerTrpGlyLeuGlyCys

538  GlyGlnLysAspValProGlyValTyrThrLysValThrAsnTyrLeuAspTrpIleArg
         | | | | | | | | | | | | | | | | | |
541  GlyGlnLysAspValProGlyValTyrThrLysValThrAsnTyrLeuAspTrpIleArg

558  AspAsnMetArgProEnd
         | | | | |
561  AspAsnMetArgProEnd
```

Matches = 556
Length = 566
Mismatches = 7
Matches/length = 98.2 percent
Unmatched = 3

TABLE 4

TPA OLIGONUCLEOTIDES

BLOCK 1 = FINGER DOMAIN
P1    5'GATCTAGATACCAAGTG
P2    5'ATCTGCAGAGATGAAAAAACGC

TABLE 4-continued
TPA OLIGONUCLEOTIDES

| | |
|---|---|
| P3 | 5'AGATGATATACCAGCAACAT |
| P4 | 5'CAGTCATGGCTGCGCCCTGTGC |
| P5 | 5'TCAGAAGCAACCGGGTGGAAT |
| P6 | 5'ATTGCTGGTGCAACAGTGGCAG |
| P7 | 5'AGCACAGTGTCACTCAGTTCCTGTTAACGCATG |
| P8 | 5'GCAGATCACTTGGTATCTA |
| P9 | 5'ATCATCTGCGTTTTTTCATCTCT |
| P10 | 5'ATGACTGATGTTGCTGGTAT |
| P11 | 5'CTTCTGAGCACAGGGCGCAGCC |
| P12 | 5'AGCAATATTCCACCCGGTTG |
| P13 | 5'TGTGCTCTGCCACTGTTGCACC |
| P14 | 5'CGTTAACAGGAACTGAGTGACAC |

BLOCK 2 = GROWTH FACTOR DOMAIN

| | |
|---|---|
| P15 | 5'CAGCGAGCCAAGGTGTTTCAACGGGGGCACC |
| P16 | 5'TGCCAGCAGGCCCTGTACTTCTCAGATTTC |
| P17 | 5'GTGTGCCAGTGCCCCGAAGG |
| P18 | 5'ATTTGCTGGGAAGTGCTGTGATAT |
| P19 | 5'GAAACACCTTGGCTCGCTGCATG |
| P20 | 5'CCTGCTGGCAGGTGCCCCCGTT |
| P21 | 5'GGCACACGAAATCTGAGAAGTACAGGG |
| P22 | 5'AGCAAATCCTTCGGGGCACT |
| P23 | 5'CGATATCACAGCACTTCCC |

BLOCK 3 = KRINGLE 1 DOMAIN

| | |
|---|---|
| P24 | 5'CGATACCCGGGCCACGTGCTAC |
| P25 | 5'GAGGACCAGGGCATCAGCTACAGG |
| P26 | 5'GGCACGTGGAGCACAGCGGAG |
| P27 | 5'AGTGGCGCCGAGTGCACCAACTGGAACAG |
| P28 | 5'CAGCGCGTTGGCCCAGAAGCCCTAC |
| P29 | 5'AGCGGGCGGAGGCCAGACGCCATCA |
| P30 | 5'GGCTGGGCCTGGGGAACCACAACTACTGCAG |
| P31 | 5'AAACCCAGATCGAGACTCAAAGCCCTGGTGC |
| P32 | 5'TACGTCTTTAAGGCGGGGAAGTACAGCTCAGAG |
| P33 | 5'TTCTGCAGCACCCCTGCCTGCTCTGAGG |
| P34 | 5'GTCCTCGTAGCACGTGGCCCGGGTAT |
| P35 | 5'CGTGCCCCTGTAGCTGATGCCCTG |
| P36 | 5'CGCCACTCTCCGCTGTGCTCCA |
| P37 | 5'ACGCGCTGCTGTTCCAGTTGGTGCACTCGG |
| P38 | 5'CCCGCTGTAGGGCTTCTGGGCCA |
| P39 | 5'CCAGCCTGATGGCGTCTGGCCTCCG |
| P40 | 5'CTGGGTTTCTGCAGTAGTTGTGGTTCCCCAGGC |
| P41 | 5'AAAGACGTAGCACCAGGGCTTTGAGTCTCGAT |
| P42 | 5'GCAGAACTCTGAGCTGTACTTCCCCGCCTT |
| P43 | 5'GATCCCTCAGAGCAGGCAGGGGTGCT |

BLOCK 4 = KRINGLE 2 DOMAIN

| | |
|---|---|
| P44 | 5'GATCCGTTAACGACTGCTACTT |
| P45 | 5'TGGGAATGGGTCAGCCTACC |
| P46 | 5'GTGGCACGCACAGCCTCACCGAG |
| P47 | 5'TCGGGTGCCTCCTGCCTCCCGTGGA |
| P48 | 5'ATTCCATGATCCTGATAGGCAAG |
| P49 | 5'GTTTACACAGCACAGAACCCCAGTGCGC |
| P50 | 5'AGGCACTGGGGCTCGGGAAAC |
| P51 | 5'ATAATTACTGCCGGAATCCTGATG |
| P52 | 5'GGGATGCCAAGCCCTGGTGCCACGT |
| P53 | 5'GCTGAAGAACCGCAGGCTGACGTGG |
| P57 | 5'AAAGGAGGGCTCTTCGCCGACATCGCCT |
| P58 | 5'CCCACCCCTGGCAGGCTGC |
| P59 | 5'CATCTTTGCCAAGCACAGGAGGTCGCC |
| P60 | 5'CGGAGAGCGGTTCCTGTGCG |
| P61 | 5'GGGGCATACTCATCAGCTCCTGCTGGAT |
| P62 | 5'TCTCTCTGCCGCCCACTGCTTCCA |
| P63 | 5'GGAGAGGTTTCCGCCCCACCAC |
| P64 | 5'CTGACGGTGATCTTGGGCAGAACATAC |
| P65 | 5'CGGGTGGTCCCTGGCGAGGAGGAGCAGAAAT |
| P66 | 5'TTGAAGTCGAAAAATACATTGTCCATAAGG |
| P67 | 5'TTCCCAAAGTAGCAGTCGTTAACG |
| P68 | 5'TGCCACGGTAGGCTGACCCA |
| P69 | 5'CACCCGACTCGGTGAGGCTGTGCG |
| P70 | 5'CATGGAATTCCACGGGAGGCAGGAGG |
| P71 | 5'GTAAACCTTGCCTATCAGGAT |
| P72 | 5'AGTGCCTGCGCACTGGGGTTCTGTGCTGT |
| P73 | 5'AGTAATTATGTTTCCCGAGCCCC |
| P74 | 5'CATCCCCATCAGGATTCCGGC |
| P75 | 5'CTTCAGCACGTGGCACCAGGGCTTGG |
| P76 | 5'AGTACTCCCACGTCAGCCTGCGGTT |
| P80 | 5'CCAGGGGTGGGAGGCGATGTCGGCGAAGAGCC |
| P81 | 5'TTGGCAAAGATGGCAGCCTG |
| P82 | 5'TCTCCGGGCGACCTCCTGTGC |
| P83 | 5'ATGCCCCGCACAGGAACCGC |
| P84 | 5'AGAGAGAATCCAGCAGGAGCTGATGAGT |
| P85 | 5'CTCTCCTGGAAGCAGTGGGCGGC |

TABLE 4-continued
TPA OLIGONUCLEOTIDES

| | |
|---|---|
| P86 | 5'CGTCAGGTGGTGGGGCGGAAAC |
| P87 | 5'CACCCGGTATGTTCTGCCCAAGATCAC |
| P88 | 5'GACTTCAAATTTCTGCTCCTCCTCGCCAGGGAC |
| P89 | 5'AATTCCTTATGGACAATGTATTTTTC |
| P92 | 5'GAGTACTGTGATGTGCCCTCCTGCGCAACCGCATGC |
| P93 | 5'GGCCGGAGATACAGCCAGCCTCAGTTTCGCATC |
| P94 | 5'GGCCGCATGCGGTTGCGCAGGAGGGCACATCAC |
| P95 | 5'CTCCTTTGATGCGAAACTGAGGCTGGCTGTATCTCC |

TABLE 5

| Domains | Native TPA |
|---|---|
| TPA DOMAINS | |
| Finger | Serine #1 → Lysine #49 |
| | Nucleotides 190 → 336 |
| Growth Factor | Serine #50 → Threonine #91 |
| | Nucleotides 337 → 462 |
| Kringle 1 | Cysteine #92 → Serine #174 |
| | Nucleotides 463 → 711 |
| Kringle 2 | Glutamic acid #175 → Serine #262 |
| | Nucleotides 712 → 975 |
| Active Site | Threonine #263 → Proline #527 |
| | Nucleotides 976 → 1770 |

TABLE 5-continued

| Domains | Native TPA |
|---|---|
| TPA ANALOG (CHART 11) | |
| Finger | Serine #1 → Valine #49 |
| | Nucleotides 190 → 342 |
| Growth Factor | Alanine #51 → Alanine #91 |
| | Nucleotides 343 → 456 |
| Kringle 1 | Threonine #92 → Cysteine #175 |
| | Nucleotides 457 → 726 |
| Kringle 2 | Glutamic acid #176 → Alanine #266 |
| | Nucleotides 727 → 999 |
| Active Site | Cysteine #267 → Proline #530 |
| | Nucleotides 1000 → 1782 |

CHART 1.
THE CONSTRUCTION OF pTRZ1.

(a) pMC1403 is treated with EcoRI, Klenow enzyme and bacterial alkaline phosphatase to yield fragment 1.

Fragment 1

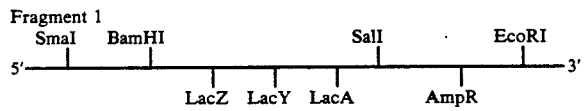

(b) pVV1 is treated with PvuII, BglII and Klenow enzyme followed by purification of fragment 2 (323 bp) containing the trp promoter and part of TrpLE.

Fragment 2

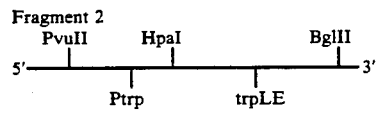

(c) Fragments 1 and 2 are ligated using T4 DNA ligase to yield pTRZ1 (10 kb).

pTRZ1

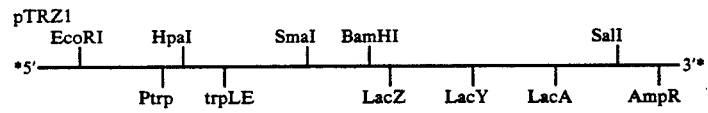

AmpR = Ampicillin resistance.
LacZ, LacY, LacA = Genes in the lactose operon.
Ptrp = Trp promoter/operator.
trpLE = Fusion of trpL and trpE.

CHART 2.
CONSTRUCTION OF pSK3 (4.3 kb).

(a) pTRZ1 (10 kb) is treated with BamHI and EcoRI and alkaline phosphatase to yield fragment 3 (350 bp).

Fragment 3

(b) pKC7 (5.8 kb) is treated with BamHI and EcoRI to yield fragment 4 (4.0 kb).

Fragment 4

-continued

CHART 2.
CONSTRUCTION OF pSK3 (4.3 kb).

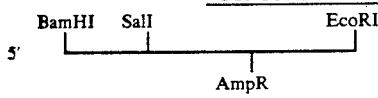

(c) Fragments 3 and 4 are ligated to form pSK3 (4.3 kb).

pSK3

D = Trp promoter/operator.
E = TrpL ribosome binding site.
F = trpLE and restriction sites.
AmpR = Ampicillin resistance.

CHART 3.
CONSTRUCTION OF pSK4.

(a) pSK3 is cut with EcoRI and BamHI to isolate fragment 5 (322 bp).

Fragment 5

(b) A partial TaqI digestion yields the 278 bp fragment 6 EcoRI to TaqI''' and other fragments.

(c) Fragment 6 is cloned into pBR322, cut with EcoRI and ClaI to yield pSK4 (4.6 kb).

pSK4

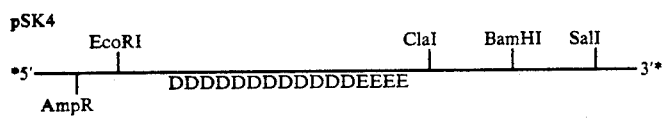

D = Trp promoter/operator.
E = Shine-Dalgarno region.

CHART 4.
CONSTRUCTION OF pTPA 3' cDNA (a) Plasmid pTPAH (5.7 kb) is obtained by cutting pBR322 with PstI, tailing and inserting the 3' region of TPAcDNA having positions 1250 to 2530.

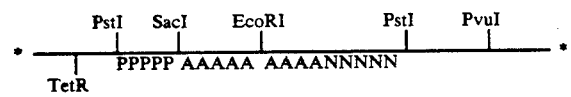

(b) Plasmid pTPA80-1 (5.4 kb) is obtained by cutting pBR322 with PstI, tailing and inserting cDNA of TPA having positions 550-1600.

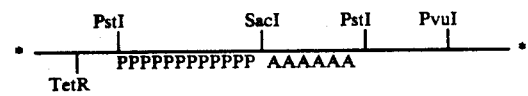

(c) Plasmid pTPAH and pTPA80-1 are cut with SacI and PvuI and fragments 7 (1251 bp) and 8 (5.1 kb) respectively are gel isolated. The fragments are treated with bacterial alkaline phosphatase and ligated with T4 to form pTPA3' cDNA (6.3 kb) having bases 550-2530 of the TPAcDNA.

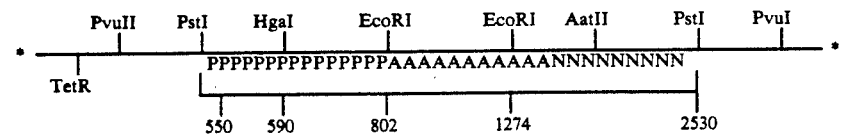

TetR = Tetracycline resistance.

-continued
CHART 4.
CONSTRUCTION OF pTPA 3' cDNA

P = 550-802 base positions of TPAcDNA.
A = 803-2530 base positions of TPAcDNA.
N = Untranslated 3' region of TPAcDNA.

CHART 5.
CONSTRUCTION OF pTPAcDNA.

(a) Plasmid pTPA 5' cDNA is obtained by cutting pBR322 with PstI, tailing and inserting the 5' region of TPAcDNA positions 1-750.

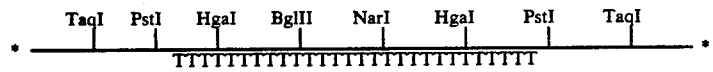

(b) Plasmid pTPA 5' is cut with TaqI to yield fragment 9 (2194 bp) with is gel isolated and cut with BglII and HgaI to yield fragment 10 (405 bp) containing bases 188 to 593 of TPAcDNA (the mature TPA protein).

Fragment 10

(c) Plasmid pTPA 3' cDNA (Chart 4) is cut with PvuII and EcoRI and fragment 11 (1748 bp) is gel isolated. Fragment 11 is cut with HgaI to yield fragment 12 (209 bp) which is gel isolated and contains bases 594 to 802.

Fragment 11
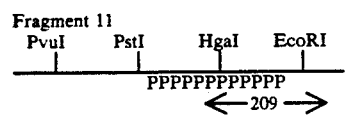

(d) Plasmid pTPA 3' cDNA is cut with PvuI, the linear 6.3 kb fragment is treated with T4 polymerase to blunt the ends, and partially digested with EcoRI to yield fragment 13 (1871 kb) containing bases 802 to 2530 plus 123 bp of pBR322.

Fragment 13

(e) Plasmid pKC7 is cut with BglII and SmaI, treated with bacterial alkaline phosphatase and fragment 14 (4.8 kb) is gel isolated.

Fragment 14
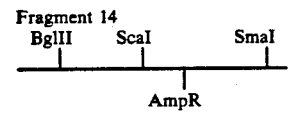

(f) Fragments 10, 12, 13 and 14 are pooled and ligated using T4 ligase to yield pTPAcDNA (7.4 kb) containing the mature TPAcDNA.

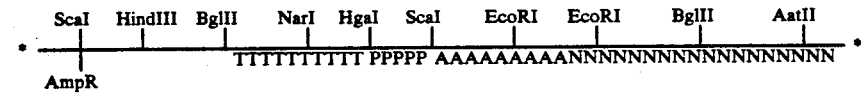

AmpR = Ampicillin resistance.
T = 5' portion of TPA cDNA.
P = Middle portion of TPA cDNA.
A = 3' portion of TPA cDNA.
N = Untranslated 3' portion of TPA cDNA.

CHART 6.
CONSTRUCTION OF pTPA-B1

(a) Plasmid pSK4 is cut with ClaI and SphI to yield fragment 15 (4.1 kb) which is isolated and ligated to Block 1 containing the finger domain through a ClaI/XbaI linker containing ATG.

Fragment 15

-continued
CHART 6.
CONSTRUCTION OF pTPA-B1

(a) 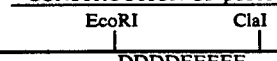

Block 1 (150 kb) 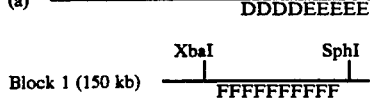

CHART 6. CONSTRUCTION OF pTPA-B1 -continued

Linker (ClaI) CGATAAGCTATGT
TATTCGATACAGATC (XbaI)

(b) Fragments 15 and Block 1 are ligated through the linker to yield pTPA-B1 (4.25 kb).

pTPA-B1

CHART 6. CONSTRUCTION OF pTPA-B1 -continued

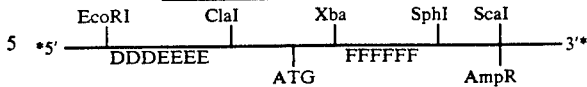

D = Trp promoter/operator.
E = TrpL ribosome binding site.
F = Finger domain.
AmpR = Ampicillin resistance.
ATG = Initiation codon.

CHART 7. CONSTRUCTION OF pTPA-B1,2

(a) Plasmid pTPA-B1 is cut with EcoRI and SphI to yield fragment 16 (450 bp) and Block 2 (100 bp) containing the growth factor domain, and is isolated from the appropriate clone using EcoRI and SphI.

Fragment 16
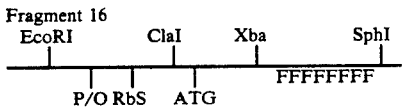

Block 2
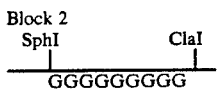

(b) Fragment 16 and Block 2 are ligated to fragment 17 (4.35 kb) derived from an EcoRI/ClaI digestion of pBR322 to yield pTPA-B1,2 (4.8 kb).

Fragment 17
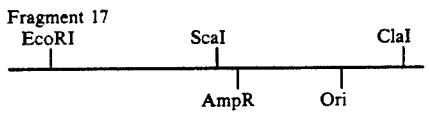

pTPA-B1,2
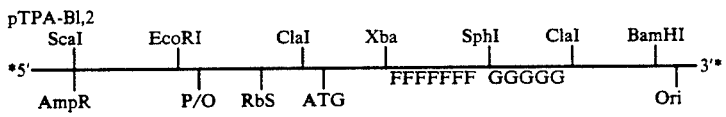

P/O = Trp promoter/operator.
RbS = Trp ribosome binding site.
ATG = Initiation codon.
F = Finger domain.
G = Growth factor domain.
AmpR = Ampicillin resistance.
Ori = Replication origin of PBR322.

CHART 8. CONSTRUCTION OF pTPA-B1,2(a)

(a) Plasmid pTPA-B 1,2 is cut with XbaI and EcoRi to yield fragment 18(4.5 kb) which was isolated and ligated to a linker containing a HindIII site and BglII site to yield pTPA-B1,2(a) (4.5 kb).

Fragment 18
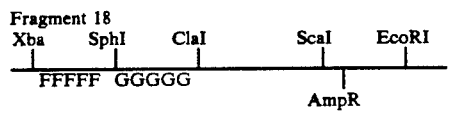

HindIII
|
Linker (EcoRI) AATTCAAGCTTAGAT
GTTCGAATCTAGATC (XbaI)
|
BglII pTPA-B1,2(a)
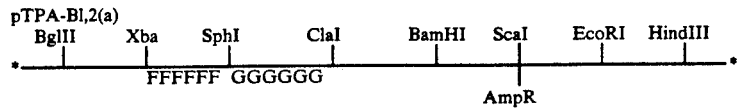

F = Finger.
G = Growth factor region.

CHART 8. CONSTRUCTION OF pTPA-B1,2(a) -continued

AmpR = Ampicillin resistance.

CHART 9. CONSTRUCTION OF pTPA-B1,2,3

Plasmid pTPA-B1,2(a) is cut with ClaI/BamHI and fragment 19 (4.0 kb) is isolated and ligated with Block 3 (270 bp) containing kringle 1 and a ClaI site upstream and a BamHI site downstream to yield pTPA3 (4.3 kb).

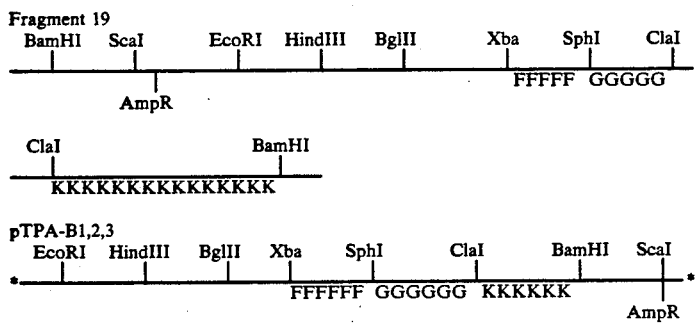

pTPA-B1,2,3

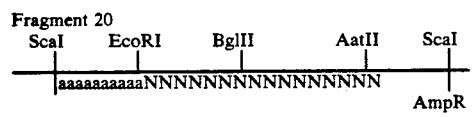

F = Finger domain.
G = Growth factor domain.
K = Kringle 1.
AmpR = Ampicillin resistance.

CHART 10. CONSTRUCTION OF pTPA-B1,2,3,4(a)

(a) Plasmid pTPAcDNA (Chart 5) is cut with ScaI and fragment 20 (6.0 kb) containing the 3' portion of the TPA gene is gel isolated.

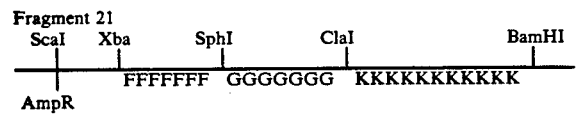

(b) Plasmid pTPA-B1,2,3 (Chart 9) is cut with ScaI and BamHI and fragment 21 (1100 bp) is gel isolated.

Fragment 21

```
ScaI   Xba    SphI        ClaI         BamHI
 |      |      |           |             |
 |      FFFFFFF GGGGGGG KKKKKKKKKKK
AmpR
```

(c) From the clone containing block 4 isolate a BamHI/ScaI fragment 4a (230 bp) containing the Kringle 2 region.

(d) Fragments 20, 21 and 4a are ligated to form pTPA-B1,2,3,4a.

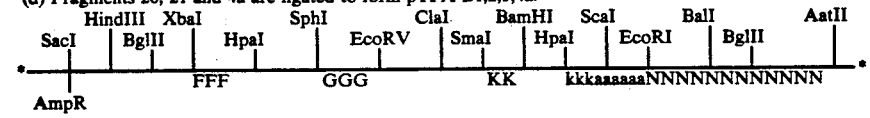

(e) Plasmid pTPA-B1,2,3,4a is cut with HindIII and AatII and the 2.2 kb prototype TPA gene is subcloned into pUC19 similarly digested with HindIII and AatII to yield pTPA-B1,2,3,4a (4.2 kb). Plasmid pTPA-B1,2,3,4a is symbolically similar to the pTPA-B1,2,3,4a but has a more convenient arrangement of restriction sites.
AmpR = Ampicillin resistance.
F = Finger domain.
G = Growth factor domain.
K = Kringle 1 domain.
k = Kringle 2 domain.
a = Active site.
N = Untranslated 3' portion of TPAcDNA.

CHART 11. CONSTRUCTION OF pTPA-B1,2,3,4

(a) Plasmid pTPA-B1,2,3,4a is cut with EcoRI and BamHI. The large fragment (3.7 kb) is ligated to block 4 (560 bp) obtained from the appropriate clone also cut with EcoRI (partial digestion) and BamHI to yield pTPA-B1,2,3,4.

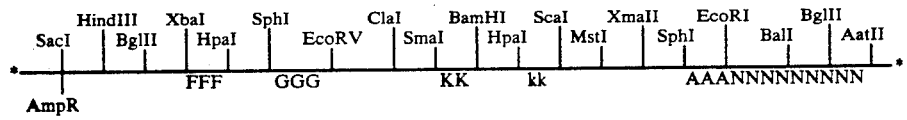

AmpR = Ampicillin resistance.
F = Finger domain.
G = Growth factor domain.
K = Kringle 1 domain.
k = Kringle 2 domain.
A = 3' portion of TPAcDNA.
N = Untranslated 3' portion of TPAcDNA.

CHART 12. CONSTRUCTION OF pFK2K2A (a) Plasmid pTPA-B1,2,3,4a is cut with HpaI to yield fragment 22 (6.5 kb) which is isolated from a gel.

Fragment 22
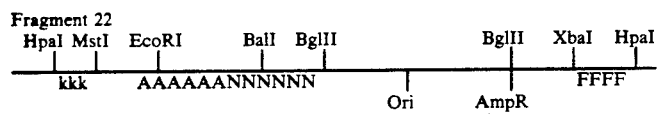

(b) Plasmid pTPA-B1,2,3,4 is cut with HpaI and MstI to yield fragment 23 (506 bp) containing kringle 2.

(c) Fragments 22 and 23 are ligated together to yield pFK2K2A (7.1 kb).

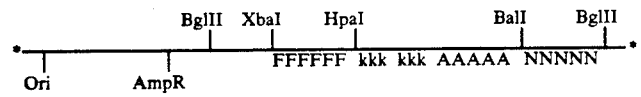

Ori = Replication origin for pBR322.
AmpR = Ampicillin resistance.
k = Kringle 2 domain.
F = Finger domain.
A = Active site.
N = Noncoding 3' sequence.

CHART 13. CONSTRUCTION OF pTPAExp 1

(a) Plasmid pTPA-B1,2 (Chart 7) is cut with XbaI and BamHI and fragment 24 (4.2 kb) which is gel isolated.

Fragment 24
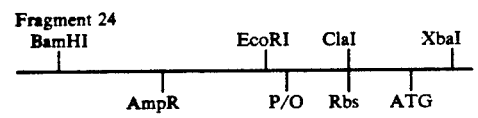

(b) Plasmid pFK2K2A (Chart 12) is cut with XbaI and BglII to yield fragment 25 (2.0 kb) which is gel isolated.

Fragment 25
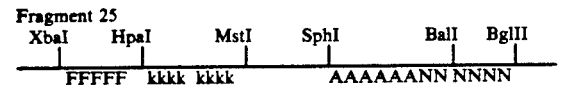

(c) Fragments 24 and 25 are ligated to form pTPAExp 1 (6.2 kb); the BamHI and BglII are complementary but are not restored.

pTPAExp 1
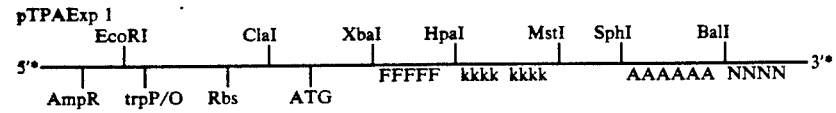

-continued
CHART 13. CONSTRUCTION OF pTPAExp 1 trpP/O = Tryptophage promoter/operator.
RbS = Ribosome binding site.
k = kringle 2.
F = Finger domain.
A = Active site.
N = Noncoding 3' sequence.
AmpR = Ampicillin resistance.
ATG = Initiation codon.

CHART 14.
CONSTRUCTION OF pyRep3'B (a) Plasmid pYIP31 is cut with SmaI and treated with bacterial alkaline phosphatase to yield fragment 26.

Fragment 26
```
       SmaI    HindIII  EcoRI    HindIII
5' ──────┼───────┼───────┼─────────┼──────── 3'
                                uuuuuuu
```

(b) The 2μ plasmid of yeast is cut with PstI and XbaI and treated with Klenow enzyme. The resulting fragment 27 (1.3 kb) is isolated.

Fragment 27
```
        PstI                   XbaI
5' ──────┼─────────────────────┼──────── 3'
         RRRRRRRRRRRRRRRR
```

(c) Fragments 26 and 27 are ligated to yield pyRep3'B (6.7 kb).

```
      EcoRI         HindIII          HindIII
*5' ────┼─────────────┼────────────────┼────── 3'*
                         uuuuuuuRRRRRRRRRR
``` u = URA3
R = Sequence spanning the RepIII and replication origin.

CHART 15.
CONSTRUCTION OF PLASMID pGG400

(a) Plasmid pBR322 is cut with EcoRI and PvuII and ends filled in with Klenow enzyme to yield fragment 28 (2.3 kb).

Fragment 28
```
        PvuII              EcoRI
5' ──────┼──────────────────┼──────── 3'
              AmpR
```

(b) Plasmid pML21 is cut with PvuII to yield fragment 29 (1.7 kb).

Fragment 29
```
        PvuII             PvuII
5' ──────┼─────────────────┼──────── 3'
              KmR
```

-continued
CHART 15.
CONSTRUCTION OF PLASMID pGG400

(c) Fragments 28 and 29 are ligated using T4 to yield pGG400 (4.0 kb).

```
      EcoRI           XhoI       PvuII
*5' ────┼──────────────┼──────────┼────── 3'*
              KmR           AmpR
```

AmpR = Ampicillin resistance.
KmR = Kanamycin resistance.

CHART 16.
CONSTRUCTION OF pADHt (a) Plasmid pGG400 is cut with XhoI and PvuII, treated with Klenow enzyme, and the resulting fragment 30 (3.5 kb) is isolated.

Fragment 30
```
       PvuII            EcoRI         XhoI
────────┼────────────────┼─────────────┼────────
              AmpR              KmR
```

(b) Plasmid pADHBC is cut with HincII and BamHI, the ends are filled with T4 ligase and the resulting fragment 31 (0.36 kb) is isolated.

Fragment 31
```
     HincII(XhoI)              SphI            BamHI
──────────┼─────────────────────┼───────────────┼──────
          HHHHHHHHHHHHHHHHHHHHHHHHHH
```

(c) Fragments 30 and 31 are ligated using T4 ligase to obtain pADHt (3.86 kb).

```
    EcoRI  HindIII  SmaI  XhoI        SphI         BamHI
* ────┼──────┼───────┼─────┼────────────┼────────────┼──── *
                          HHHHHHHHHHHHHHH
                                                AmpR
```

AmpR = Ampicillin resistance.
KmR = Kanamycin resistance.
H = ADHt 3' end.

CHART 17.
CONSTRUCTION OF PLASMID pADHt-RepIII (a) Plasmid pADHt is modified by restriction with BamHI and ligation of an 8-mer SalI linker into the filled BamHI site.

```
   EcoRI  HindIII    XhoI      SphI        SalI
* ───┼──────┼─────────┼─────────┼────────────┼──── *
                              HHHHHHHHHHHHHHH
                                            AmpR
```

(b) Plasmid pADHt (modified) is cut with SphI and the ends filled in with T4 ligase to yield fragment 32 (3.8 kb).

(c) Plasmid pyRep31B (Chart 16) is cut with HindIII and the ends filled in with T4 ligase to yield fragment 33 (2.4 kb).

```
     HindIII                                    HindIII
────────┼───────────────────────────────────────────┼────────
         uuuuuuuuuuuuuuuuuRRRRRRRRRRRRRRRR
```

CHART 17.
CONSTRUCTION OF PLASMID pADHt-RepIII (d) Fragments 32 and 33 are ligated using T4 ligase to obtain pADHt-RepIII (6.2 kb).

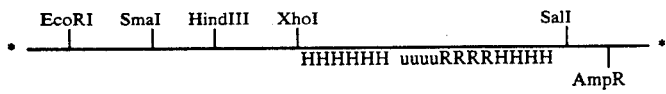

AmpR = Ampicillin resistance.
H = ADHt 3'end.
u = Ura3
R = RepIII and origin of replication

CHART 18.
CONSTRUCTION OF pαl-ADHt (a) Plasmid pADHt-RepIII (Chart 15) is cut with EcoRI and HindIII and fragment 34 (5.3 kb) is isolated.

Fragment 34
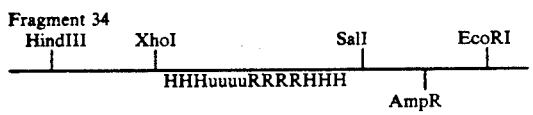

(b) Plasmid pαl is restricted with EcoRI and HindIII to yield the MFαl gene containing fragment 35 having 1.2 kb.

Fragment 35

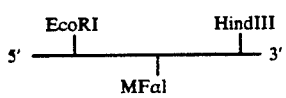

-continued
CHART 18.
CONSTRUCTION OF pαl-ADHt (c) Fragments 34 and 35 are ligated using T4 ligase to obtain pαl-ADHt (6.5 kb).

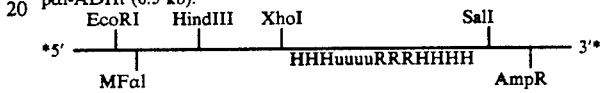

AmpR = Ampicillin resistance.
H = ADHt 3' end.
u = Ura3.
R = RepIII and origin of replication
MFαl = Promoter and signal sequence for MFαl gene.

CHART 19.
CONSTRUCTION OF pαl-FK2K2A (a) Plasmid pFK2K2A (Chart 12) is cut with BglII to obtain fragment 36 (2.0 kb) which is gel isolated.

Fragment 36
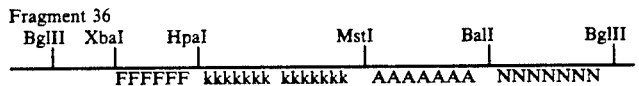

(b) Plasmid pαl-ADHt is cut with HindIII and XhoI; the ends are partially filled with Klenow enzyme in the presence of bases adenosine and guanosine, and treated with Mung Bean nuclease to yield fragment 37 (5.6 kb) which is gel isolated.

Fragment 37

(c) Fragments 36 and 37 are ligated to form pαl-FK2K2A (7.6 kb).

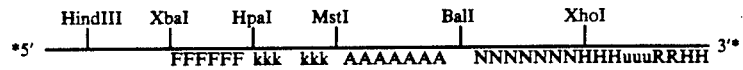

MFαl = Promoter and signal sequence for MFαl gene.
F = Finger.
k = Kringle region 2.
A = Active site.
N = Untranslated 3' sequence.
H = ADHt 3' end.
u = URA3
R = RepIII and origin of replication.

CHART 20.
CONSTRUCTION OF pSVCOW7

(a) Plasmid pSV2dhfr is cut with BamHI and EcoRI to obtain fragment 38 (5.0 kb).

Fragment 38

CHART 20.
CONSTRUCTION OF pSVCOW7

```
BamHI    PvuII    HindIII         EcoRI
  |        |        |               |
  |_____|_____|_____|
       dhfr    SV40       AmpR
```

(b) Plasmid pλGH2R2 is cut with BamHI and EcoRI to obtain fragment 39 (2.1 kb).

Fragment 39
```
EcoRI   PvuII           PstI                    BamHI
  |       |              |                        |
  |_____|_____|_____|
      AAAGGGIIIGGGGGGGGGGGGGGGGGGGGGGGGGGG
```

(c) Fragments 38 and 39 are ligated to yield pSVCOW7 (7.1 kb).

pSVCOW7
```
    EcoRI  PvuII    PstI    BamHI    PvuII    HindIII
      |      |       |        |        |        |        *
*_____|_____|_____|_____|_____|_____|_____
        AAAGGGIIGGGGGGGGGG
                              dhfr     SV40     AmpR
```

A = Bovine growth hormone poly A tail.
G = Genomic bovine growth hormone.
I = Intron.
dhfr = Dihydrofolate reductase.
SV40 = SV40 promoter and origin of replication.
AmpR = Ampicillin resistance.

CHART 21.
CONSTRUCTION OF pTPAcDNA, BamHI (a) Plasmid pTPA5'cDNA (Chart 5, part a) is cut with Hga and fragment 40 (517 bp) is made flush with Klenow and ligated to a 10-mer BamHI linker. Fragment 40 is cut with NarI to yield fragment 41 (440 bp) having bases 78 to 518 of the TPAcDNA.

Fragment 40
```
BamHI        BglII              NarI    BamHI
  |            |                  |       |
  |_____|_____|_____|
    LLLTTTTTTTTTTTTTTTTTTTTTTTTT
     ←        440         →
```

(b) Plasmid pTPAcDNA (Chart 5) is cut with NarI and BglII and fragment 42 (1644 bp) containing the 3' portion of TPAcDNA which is gel isolated.

Fragment 42

```
NarI    HgaI        EcoRI       EcoRI              BglII
  |       |           |           |                  |
  |_____|_____|_____|_____|
    PPPPPPPPPPPPPPP      AAAAAAAAAANNNNNNNNN
```

(c) Plasmid pKC7 is cut with BamHI and BglII to yield fragment 43 (4.3 kb) which is gel isolated and ligated with fragments 41 and 42 to yield pTPAcDNA, BamHI (6.5 kb).

pTPAcDNA, BamHI
```
    BamHI  BglII                    BalI       BglII
      |      |                        |          |           *
*_____|_____|_____|_____|_____
       LLLLTTTTPPPPAAAANNNNN   NNNNNN
                                                    AmpR
```

L = Leader sequence.
T = 5' portion of TPAcDNA.
P = Middle portion of TPAcDNA.
A = 3' portion of TPAcDNA.
N = Untranslated 3' portion of TPAcDNA.

CHART 22.
CONSTRUCTION OF pTPA-IE-PA (a) Plasmid pSVCOW7 is cut with EcoRI and PvuII to yield fragment 44 (600 bp) containing the polyadenylation sequence of bovine growth hormone which is gel isolated.

Fragment 44
```
EcoRI              PvuII
  |                  |
  |_____|
    aaaaaaaaaaaaaaaaaa
```

(b) Plasmid pSVCOW7 (Chart 20) is cut with EcoRI and BamHI to yield fragment 45 (5.8 kb).

Fragment 45
```
BamHI                          EcoRI
  |                              |
  |_____|
      dhfr   SV40    Ori    AmpR
```

(c) Plasmid pTPAcDNA, BamHI (Chart 21) is cut with BamHI and BalI to yield fragment 46 (2.0 kb).

Fragment 46

CHART 22.
CONSTRUCTION OF pTPA-IE-PA

```
BamHI    BglII                              BalI
  |        |                                  |
  └────────┴──────────────────────────────────┘
    LLLLLTTTTTPPPPPAAAAANNNNNNNNNNNNNNNNNN
```

(d) Fragments 44, 45 and 46 are ligated to form pTPA-PA (8.4 kb).

pTPA-PA
```
  EcoRI              BamHI   BglII      BalI
    |                  |       |          |
*───┴──┬────┬─────┬────┴───────┴──────────┴─ *
                        LLLTTTTTPPPAAANNNNNaaa
    AmpR  Ori  SV40  dhfr
```

Plasmid pTPA-PA is cut with BamHI and the CMV-IE promoter (760 bp) from a PstI and Sau3AI digestion of the CMV genome is inserted to form pTPA-IE-PA.

pTPA-IE-PA
```
   EcoRI              Sau3A BalI Sau3A BamHI  BglII
     |                  |    |     |    |       |
*5'──┴──┬────┬─────┬────┴────┴─────┴────┴───────┴─ 3'*
                                       LLLL TTPPAA NNNNaaa
     AmpR  Ori  SV40  dhfr           CMV
```

AmpR = Ampicillin resistance.
Ori = pBR322 origin of replication.
SV40/ori = Simian virus origin of replication.
Mo/dhfr = Mouse dihydrofolate reductase marker.
CMV/Prom = Cytomegalovirus promoter.
L = TPA leader sequence.
T = 5' region of TPAcDNA.
P = Middle region of TPAcDNA.
A = 3' region of TPAcDNA.
N = Untranslated 3' region of TPAcDNA.
a = Polyadenylation signal sequence.

CHART 23.
CONSTRUCTION OF pTPA-IE-FK2K2A (a) pTPA-IE-PA (Chart 22) is cut with BamHI and BglII to yield fragment 47 (120 bp) which is gel isolated.

Fragment 47
```
BalI                    BglII
  |                       |
  └───────────────────────┘
   LLLLLLLLLLLLLLLLLLLLLLLLLL
```

(b) Plasmid pSVCOW7 is cut with EcoRI and PvuII to yield fragment 48 (600 bp) containing the polyadenylation sequence of bovine growth hormone which is gel isolated.

Fragment 48
```
EcoRI      PvuII
  |          |
  └──────────┘
   aaaaaaaaaaaaaaaaa
```

(c) Plasmid pFK2K2A (Chart 12) is cut with BhlII and BalI to obtain fragment 49 (1.7 kb) which is gel isolated.

Fragment 49
```
BglII  XbaI   HpaI   MstI              BalI
  |     |      |      |                  |
  └─────┴──────┴──────┴──────────────────┘
        FFFFFF  kkk kkk AAAAAANNNNNNNN
```

(d) Plasmid pSVCOW7 (Chart 20) is cut with EcoRI and BamHI to yield fragment 50.

Fragment 50
```
BamHI                 EcoRI
  |                     |
  └──┬─────┬─────┬──────┘
    dhfr  SV40  Ori   AmpR
```

(e) Fragments 47, 48, 49 and 50 are ligated using T4 ligase to yield pTPAFK2K2A (8.3 kb).

pTPAFK2K2A
```
   EcoRI              BamHI BglII  MstI
     |                  |     |     |
*5'──┴──┬────┬─────┬────┴─────┴─────┴──── 3'*
                         LLLLL FF kk kk AANNaaa
     AmpR  Ori  SV40  dhf4
```

CHART 23.
CONSTRUCTION OF pTPA-IE-FK2K2A (f) Plasmid pTPAFK2K2A is cut with BamHI and the CMV-IE promoter (760 bp) from a PstI and Sau3AI digestion of the CMV genome is inserted to form pTPA-IE-FK2K2A.

pTPA-IE-FK2K2A

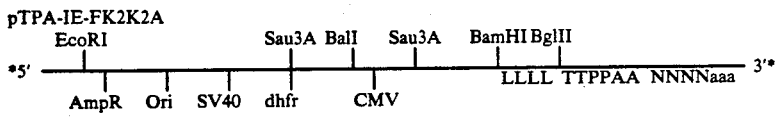

AmpR = Ampicillin resistance.
Ori = pBR322 origin of replication.
SV40 = Simian virus origin of replication.
Mo/dhfr = Mouse dihydrofolate reductase marker.
CMV/Prom = Cytomegalovirus promoter.
L = TPA leader sequence.
T = 5' region of TPAcDNA.
P = Middle region of TPAcDNA.
F = Finger domain.
k = Kringle 2.
A = Active site.
N = Untranslated 3' region of TPAcDNA.
a = Polyadenylation signal sequence.

CHART 24.
CONSTRUCTION OF pAcTPA (a) Plasmid pAc373 (7.1 kb) is cut with BamHI and treated with mung bean nuclease to create blunt ends to which BglII linkers are added. The ends are rejoined to yield pAc373, BglII.

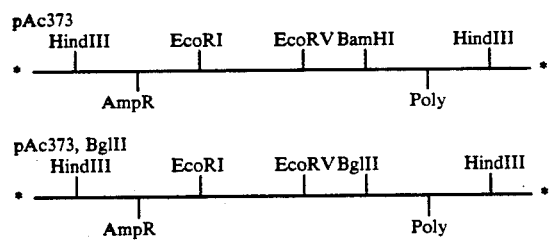

(b) Plasmid pTPAcDNA, BamHI (Chart 21) is cut with BamHI and partially digested with BglII to yield fragment 51 (1.95 kb) containing an intact TPAcDNA.

-continued
CHART 24.
CONSTRUCTION OF pAcTPA

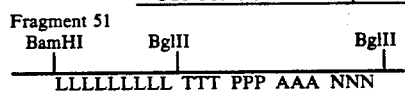

(c) Fragment 51 is inserted and ligated to the BglII site of pAc373, BglII to yield pAcTPA (9.05 kb).

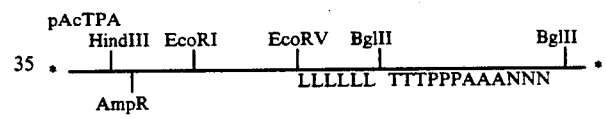

L = Leader sequence.
T = 5' portion of TPAcDNA.
P = Middle portion of TPAcDNA.
A = 3' portion of TPAcDNA.
N = Untranslated 3' portion of TPAcDNA.
AmpR = Ampicillin resistance.
Poly = Polyhedrin protein gene.

CHART 25.
CONSTRUCTION OF pAc FK2K2A (a) pAcTPA (Chart 24) is cut with BglII to yield fragment 52 (7.15 kb).

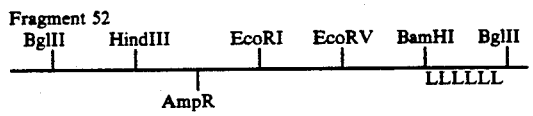

(b) Plasmid pFK2K2A (Chart 12) is cut with BglII and the analog cDNA is gel isolated as fragment 53 (2.0 kb).

(c) Fragments 52 and 53 are ligated to form pAcFK2K2A (9.15 kb).

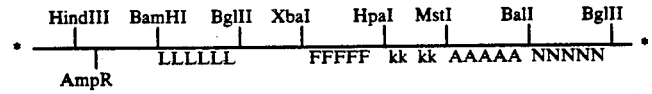

L = Leader sequence.
F = Finger domain.

CHART 25.
CONSTRUCTION OF pAc FK2K2A k = Kringle 2 domain.
A = Active site domain.
N = Untranslated 3' portion of TPAcDNA.
AmpR = Ampicillin resistance.

We claim:

1. A recombinant DNA molecule encoding a tPA analog consisting of a tPA active site A, a tPA finger domain F and a tPA kringle 2 domain K2 wherein said recombinant DNA molecule contains non-native restriction endonuclease sites within sequences encoding interdomain regions.

2. A recombinant DNA molecule according to claim 1 encoding a tPA analog in which said domains, as ordered from the amino terminal end, are F,K2, and A.

3. A host cell comprising a recombinant DNA molecule according to claim 1, said host cell selected from the group consisting of:
   a. a yeast cell,
   b. a eukaryotic cell, and
   c. an *E. coli* cell.

4. A host cell according to claim 3 wherein said host cell is a chinese hamster ovary cell.

5. A tPA analog consisting of:
   a) a tPA active site A;
   b) a tPA active domain F; and
   c) a tPA kringle 2 domain K2.

6. A tPA analog according to claim 5 which is KK2 A.

* * * * *